United States Patent
Sakurai et al.

(10) Patent No.: US 12,276,022 B2
(45) Date of Patent: Apr. 15, 2025

(54) ALKOXIDE COMPOUND, THIN-FILM FORMING RAW MATERIAL, AND METHOD OF PRODUCING THIN-FILM

(71) Applicant: ADEKA CORPORATION, Tokyo (JP)

(72) Inventors: Atsushi Sakurai, Tokyo (JP); Masako Hatase, Tokyo (JP); Nana Okada, Tokyo (JP); Ryota Fukushima, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 18/014,371

(22) PCT Filed: Jun. 25, 2021

(86) PCT No.: PCT/JP2021/024110
§ 371 (c)(1),
(2) Date: Jan. 4, 2023

(87) PCT Pub. No.: WO2022/009695
PCT Pub. Date: Jan. 13, 2022

(65) Prior Publication Data
US 2023/0304154 A1 Sep. 28, 2023

(30) Foreign Application Priority Data
Jul. 9, 2020 (JP) .................................. 2020-118133

(51) Int. Cl.
*C23C 16/455* (2006.01)
*C23C 16/18* (2006.01)

(52) U.S. Cl.
CPC ........ *C23C 16/45553* (2013.01); *C23C 16/18* (2013.01)

(58) Field of Classification Search
CPC ......... C23C 16/06; C23C 16/18; C23C 16/24; C23C 16/301; C23C 16/325; C23C 16/345; C23C 16/401; C23C 16/402; C23C 16/403; C23C 16/405; C23C 16/406; C23C 16/407; C23C 16/408; C23C 16/45525; C23C 16/45553; C07F 1/02; C07F 1/08; C07F 3/003; C07F 3/06; C07F 5/003; C07F 5/06; C07F 5/066; C07F 5/069; C07F 7/002; C07F 7/003; C07F 7/02; C07F 7/22; C07F 7/28; C07F 7/30; C07F 7/2224; C07F 11/005; C07F 13/005; C07F 15/004; C07F 15/025; C07F 15/045; C07F 15/065; C07F 17/02; C07F 19/005
See application file for complete search history.

(56) References Cited

U.S. PATENT DOCUMENTS

| | | | | |
|---|---|---|---|---|
| 6,369,256 B1 * | 4/2002 | Chi | ........................ | C23C 16/18 556/113 |
| 7,501,153 B2 * | 3/2009 | Yamada | .................. | C23C 16/40 106/287.18 |
| 7,714,155 B2 * | 5/2010 | Sato | ...................... | C07C 215/08 427/255.28 |
| 9,994,593 B2 * | 6/2018 | Yoshino | .................. | C23C 16/18 |
| 10,118,940 B2 * | 11/2018 | Wada | ................. | C23C 16/45553 |
| 10,468,261 B2 | 11/2019 | Vayrynen et al. | | |
| 2007/0122947 A1 * | 5/2007 | Sakurai | ................... | C23C 16/18 438/572 |
| 2013/0330473 A1 * | 12/2013 | Winter | .............. | C23C 16/45553 75/392 |
| 2017/0050998 A1 * | 2/2017 | Yoshino | .................. | C07F 15/06 |
| 2020/0140463 A1 * | 5/2020 | Okada | ..................... | H01L 21/31 |

FOREIGN PATENT DOCUMENTS

| | | |
|---|---|---|
| JP | 2003-535839 | 12/2003 |
| JP | 2006-312600 | 11/2006 |

(Continued)

OTHER PUBLICATIONS

Hwang et al., "Strategy of solution process precursors for phase change memory," Polyhedron, vol. 176, 114289 (available online Dec. 12, 2019) (Year: 2019).*
Gerald Burns, Solid State Physics 339-40 (1985). (Year: 1985).*
Partial machine translation of office action issued in TW110124954, 5 pages. (Year: 2024).*
Adrian-Alexandru Somesan et al., "Aminofluoroalkoxide amido and boryloxo lead(II) complexes", Dalton Transactions, 2019, vol. 48, pp. 9944-9948. (Year: 2019).*
International Search Report (ISR) issued Sep. 7, 2021 in International (PCT) Application No. PCT/JP2021/024110.

(Continued)

*Primary Examiner* — William P Fletcher, III
(74) *Attorney, Agent, or Firm* — Wenderoth, Lind & Ponack, L.L.P.

(57) ABSTRACT

A method for producing a thin-film containing a metal atom or a semimetal atom on the surface of a substrate, comprising the steps of vaporizing a thin-film forming raw material comprising an alkoxide compound represented by the following general formula (1), introducing the vaporized compound into a treatment atmosphere, and subjecting the vaporized compound to decomposition and/or a chemical reaction, to thereby form the thin-film containing a metal atom or a semimetal atom on the surface of the substrate:

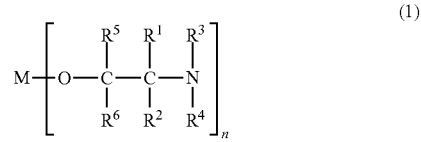

(1)

where $R^1$ to $R^6$, M and n are defined herein.

1 Claim, 2 Drawing Sheets

(56) References Cited

FOREIGN PATENT DOCUMENTS

JP          2006-328019        12/2006
JP          2018-133569         8/2018

OTHER PUBLICATIONS

Jeong Min Hwang et al., "Strategy of solution process precursors for phase change memory", Polyhedron, vol. 176, 114289, pp. 1-6, Jan. 15, 2020, cited in ISR.

Adrian-Alexandru Someşan, et al., "Aminofluoroalkoxide amido and boryloxo lead(II) complexes", Dalton Transactions, 2019, vol. 48, pp. 9944-9948.

\* cited by examiner

[Fig.1]
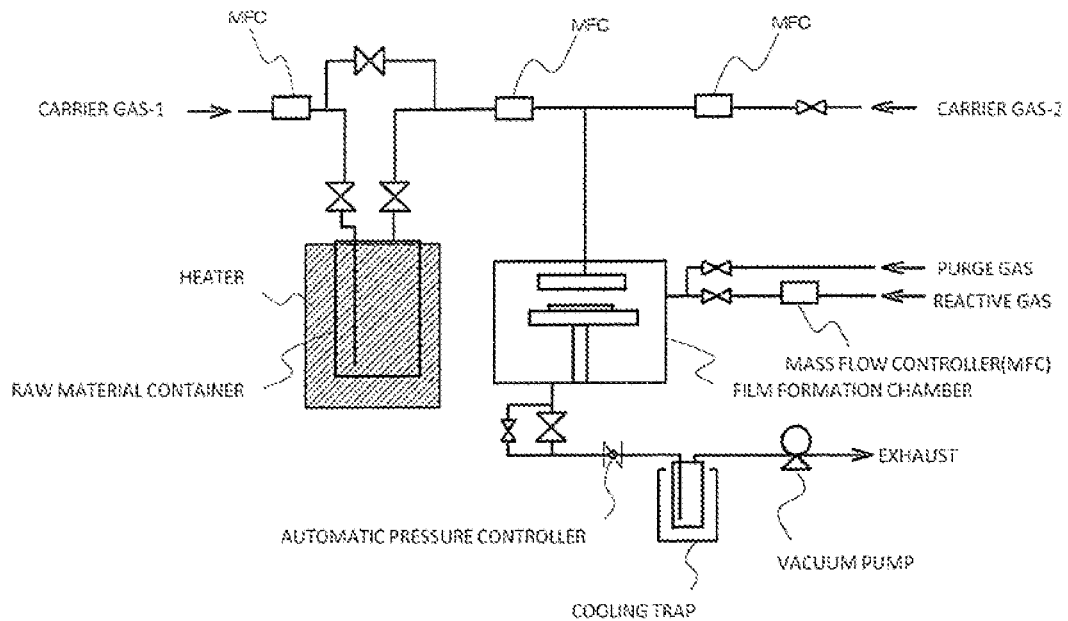
[Fig 2]
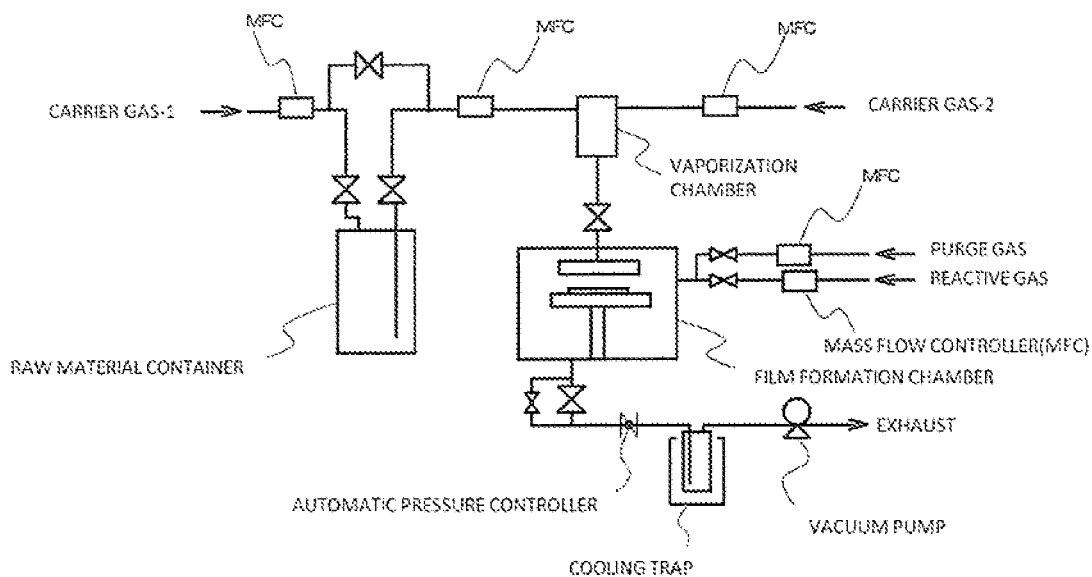

[Fig.3]
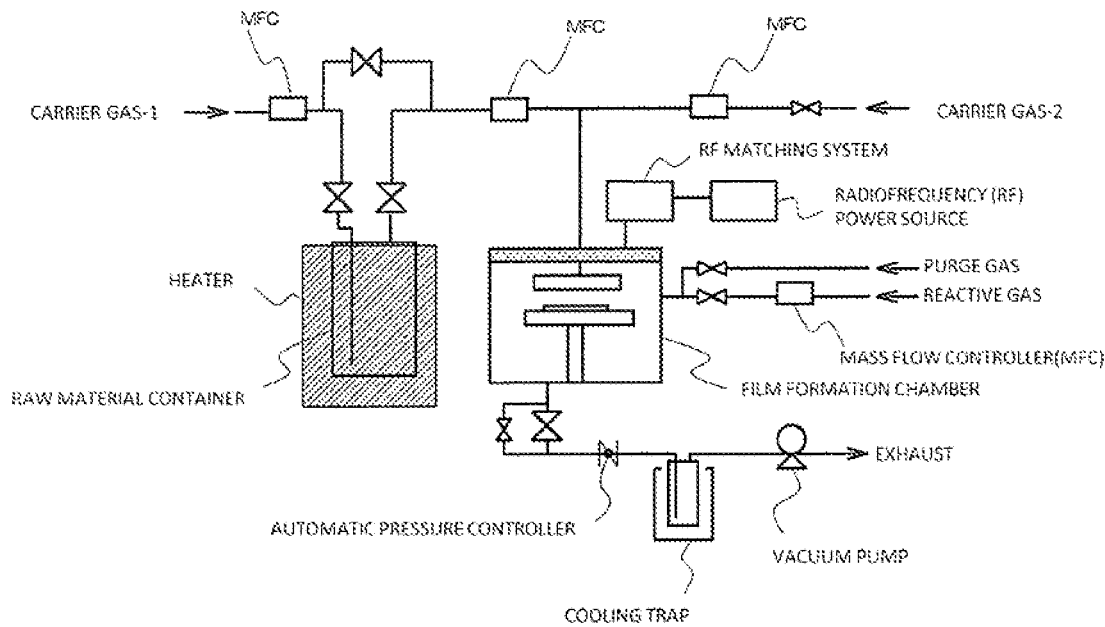
[Fig.4]
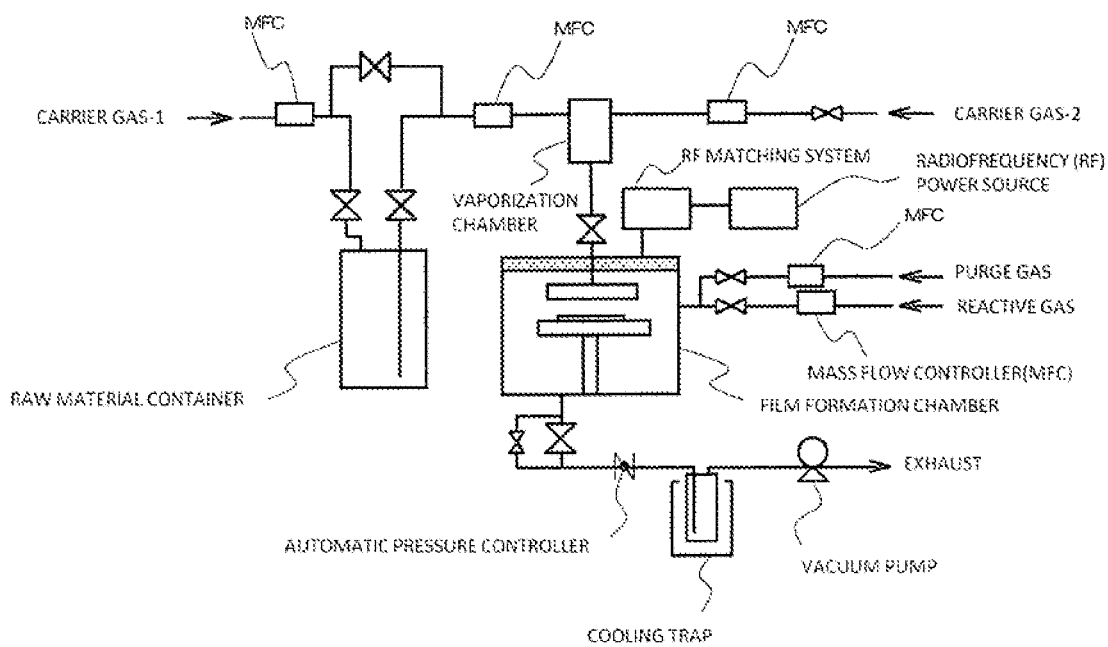

ALKOXIDE COMPOUND, THIN-FILM FORMING RAW MATERIAL, AND METHOD OF PRODUCING THIN-FILM

TECHNICAL FIELD

The present invention relates to a novel compound, a thin-film forming raw material containing the compound, and a method of producing a thin-film including using the thin-film forming raw material.

BACKGROUND ART

A thin-film material containing a metal element or a semimetal atom has been used in, for example, a member for an electronic part, such as an electrode film, a resistance film, or a barrier film, a member for recording media such as a magnetic film, or an electrode member for a solar cell thin-film or the like because of its excellent electrical characteristics and optical characteristics.

As a method of producing the thin-film, there are given, for example, a sputtering method, an ion plating method, metal organic decomposition (MOD) methods, such as a coating thermal decomposition method and a sol-gel method, and chemical vapor deposition methods. Of those, chemical vapor deposition (hereinafter sometimes simply referred to as "CVD") methods including an atomic layer deposition (ALD) method are optimum production processes because the methods each have many advantages, such as excellent composition controllability and step coverage, suitability for mass production, and capability of hybrid integration.

Various compounds have been reported as alkoxide compounds to be used in the chemical vapor deposition method. In, for example, Patent Document 1, there are disclosures of an aminoalkoxide-titanium compound, an aminoalkoxide-zirconium compound, and an aminoalkoxide-hafnium compound. In addition, in Patent Document 2, there is a disclosure of an aminoalkoxide-copper compound. In Patent Document 3, there are disclosures of an aminoalkoxide-copper compound, an aminoalkoxide-nickel compound, and an aminoalkoxide-cobalt compound.

CITATION LIST

Patent Documents

[Patent Document 1] JP 2006-312600 A
[Patent Document 2] JP 2006-328019 A
[Patent Document 3] JP 2018-133569 A

SUMMARY OF INVENTION

Technical Problem

In a method including vaporizing a compound to form a thin-film such as the CVD method, the compound (precursor) to be used as a raw material is particularly required to have the following properties: the compound has a large vapor pressure; the compound has a low melting point (the compound is preferably a liquid at normal temperature); the compound has high thermal stability; and the compound can produce a high-quality thin-film with satisfactory productivity. A thin-film forming raw material containing an alkoxide compound has been required to have the following properties out of the properties: the compound has a large vapor pressure; the compound has high thermal stability; and the compound can produce a high-quality thin-film with satisfactory productivity when used as a thin-film forming raw material. However, an alkoxide compound capable of sufficiently satisfying those properties has not heretofore existed.

Accordingly, an object of the present invention is to provide an alkoxide compound, which has a large vapor pressure, has high thermal stability, and can produce a high-quality thin-film with satisfactory productivity when used as a thin-film forming raw material as compared to the related-art alkoxide compound.

Solution to Problem

The inventors of the present invention made investigations, and as a result, found that an alkoxide compound having a ligand having a specific structure can solve the above-mentioned problem. Thus, the inventors have reached the present invention.

That is, the present invention relates to an alkoxide compound represented by the following general formula (1):

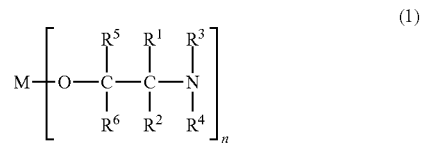

where $R^1$ and $R^2$ each independently represent a hydrogen atom, an alkyl group having 1 to 5 carbon atoms, or a fluorine atom-containing alkyl group having 1 to 5 carbon atoms, $R^3$ and $R^4$ each independently represent an alkyl group having 1 to 5 carbon atoms, or a fluorine atom-containing alkyl group having 1 to 5 carbon atoms, $R^5$ represents a hydrogen atom, a fluorine atom-containing group, or an alkyl group having 1 to 5 carbon atoms, $R^6$ represents a fluorine atom-containing group, M represents a metal atom or a semimetal atom, and "n" represents a valence of the atom represented by M, provided that when M represents a copper atom, $R^3$ and $R^4$ each independently represent an alkyl group having 1 or 2 carbon atoms, and $R^5$ represents a hydrogen atom.

The present invention also relates to a thin-film forming raw material, comprising the above-mentioned compound.

The present invention also relates to a method of producing a thin-film, comprising the steps of: vaporizing the above-mentioned thin-film forming raw material; introducing vapor containing the alkoxide compound represented by the general formula (1), which has been vaporized, into a treatment atmosphere; and subjecting the compound to decomposition and/or a chemical reaction, to thereby form a thin-film containing a metal atom or a semimetal atom on a surface of a substrate.

An alkoxide compound represented by the following general formula (2) is identical in meaning to the alkoxide compound represented by the general formula (1):

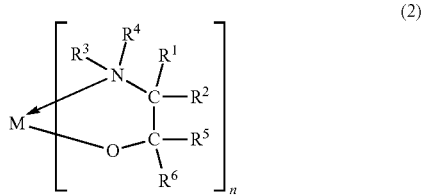

(2)

where $R^1$ and $R^2$ each independently represent a hydrogen atom, an alkyl group having 1 to 5 carbon atoms, or a fluorine atom-containing alkyl group having 1 to 5 carbon atoms, $R^3$ and $R^4$ each independently represent an alkyl group having 1 to 5 carbon atoms, or a fluorine atom-containing alkyl group having 1 to 5 carbon atoms, $R^5$ represents a hydrogen atom, a fluorine atom-containing group, or an alkyl group having 1 to 5 carbon atoms, $R^4$ represents a fluorine atom-containing group, M represents a metal atom or a semimetal atom, and "n" represents a valence of the atom represented by M, and in each of $R^3$ to $R^4$, part or all of hydrogen atoms of the alkyl group may be substituted with a fluorine atom, provided that when M represents a copper atom, $R^3$ and $R^4$ each independently represent an alkyl group having 1 or 2 carbon atoms, and $R^5$ represents a hydrogen atom.

Advantageous Effects of Invention

According to the present invention, the alkoxide compound, which has a large vapor pressure, has high thermal stability, and can produce a high-quality thin-film with satisfactory productivity when used as a thin-film forming raw material as compared to the related-art alkoxide compound, can be provided. The compound of the present invention is suitable as a thin-film forming raw material for a CVD method. In particular, the compound has an ALD window, and hence can be preferably used as a thin-film forming raw material to be used for an ALD method.

BRIEF DESCRIPTION OF DRAWINGS

FIG. 1 is a schematic diagram for illustrating an ALD apparatus to be used in a method of producing a thin-film according to one embodiment of the present invention.

FIG. 2 is a schematic diagram for illustrating the ALD apparatus to be used in the method of producing a thin-film according to another embodiment of the present invention.

FIG. 3 is a schematic diagram for illustrating the ALD apparatus to be used in the method of producing a thin-film according to still another embodiment of the present invention.

FIG. 4 is a schematic diagram for illustrating the ALD apparatus to be used in the method of producing a thin-film according to yet still another embodiment of the present invention.

DESCRIPTION OF EMBODIMENTS

An alkoxide compound of the present invention is represented by the general formula (1). The alkoxide compound of the present invention is suitable as a precursor in a method of producing a thin-film comprising a vaporization step such as an ALD method, which is one kind of CND method.

In the general formula (1), $R^1$ and $R^2$ each independently represent a hydrogen atom, an alkyl group having 1 to 5 carbon atoms, or a fluorine atom-containing alkyl group having 1 to 5 carbon atoms, $R^3$ and $R^4$ each independently represent an alkyl group having 1 to 5 carbon atoms, or a fluorine atom-containing alkyl group having 1 to 5 carbon atoms, $R^5$ represents a hydrogen atom, a fluorine atom-containing group, or an alkyl group having 1 to 5 carbon atoms, $R^6$ represents a fluorine atom-containing group, M represents a metal atom or a semimetal atom, and "n" represents the valence of the atom represented by M, provided that when M represents a copper atom, $R^3$ and $R^4$ each independently represent an alkyl group having 1 or 2 carbon atoms, and $R^1$ represents a hydrogen atom.

Specific examples of the "alkyl group having 1 to 5 carbon atoms" in each of $R^1$ to $R^5$ described above include a methyl group, an ethyl group, a propyl group, an isopropyl group, a butyl group, an isobutyl group, a sec-butyl group, a tert-butyl group, a pentyl group, an isopentyl group, and a neopentyl group.

The "fluorine atom-containing alkyl group having 1 to 5 carbon atoms" in each of $R^1$ to $R^4$ described above refers to an alkyl group obtained by substituting part or all of the hydrogen atoms of an alkyl group having 1 to 5 carbon atoms with a fluorine atom. Specific examples of the fluorine atom-containing alkyl group include a fluoromethyl group, a difluoromethyl group, a trifluoromethyl group, a 2,2,2-trifluoroethyl group, a 1,1,2,2,2-pentafluoroethyl group, a 3,3,3-trifluoropropyl group, a 2,2,3,3,3-pentafluoropropyl group, a 1,1,2,2,3,3,3-heptafluoropropyl group, a 4,4,4-trifluorobutyl group, a 3,3,4,4,4-pentafluorobutyl group, a 2,2,3,3,4,4,4-heptafluorobutyl group, and a 1,1,2,2,3,3,4,4,4-nonafluorobutyl group.

The "fluorine atom-containing group" in each of $R^5$ and $R^6$ described above refers to a fluoro group or a fluorine atom-containing alkyl group having 1 to 5 carbon atoms. Specific examples of the "fluorine atom-containing alkyl group having 1 to 5 carbon atoms" in this case are the same as the specific examples of the "fluorine atom-containing alkyl group having 1 to 5 carbon atoms" in each of $R^1$ to $R^4$.

Examples of the metal atom or the semimetal atom represented by M described above include a copper atom, a cobalt atom, a nickel atom, a tin atom, a zinc atom, an yttrium atom, an iron atom, an indium atom, a gallium atom, an aluminum atom, a titanium atom, a germanium atom, a zirconium atom, a hafnium atom, and a silicon atom.

In the general formula (1), $R^1$ to $R^6$ and M are each appropriately selected in accordance with a method of producing a thin-film to which the compound is applied. When the compound is used in a method of producing a thin-film comprising the step of vaporizing the compound, it is preferred to select $R^1$ to $R^6$ and M so that the compound has a large vapor pressure and high thermal stability.

$R^1$ and $R^2$ in the general formula (1) each represent preferably a hydrogen atom or an alkyl group having 1 to 3 carbon atoms, more preferably a hydrogen atom or a methyl group, particularly preferably a hydrogen atom because the compound has a large vapor pressure. $R^3$ and $R^4$ in the general formula (1) each represent preferably an alkyl group having 1 to 3 carbon atoms, more preferably a methyl group or an ethyl group because the compound has high thermal stability. A case in which $R^3$ represents a methyl group and $R^4$ represents an ethyl group is particularly preferred. $R^5$ in the general formula (1) represents preferably a hydrogen atom or a fluorine atom-containing group, more preferably a hydrogen atom because the compound has a large vapor pressure. $R^6$ in the general formula (1) represents preferably a monofluoromethyl group, a difluoromethyl group, a trifluoromethyl group, a 2,2,2-trifluoroethyl group, or a 3,3,3- trifluoropropyl group, more preferably a trifluoromethyl group, a 2,2,2-trifluoroethyl group, or a 3,3,3-trifluoropropyl group, particularly preferably a trifluoromethyl group because the compound has a large vapor pressure and high thermal stability.

M in the general formula (1) represents preferably a copper atom, a cobalt atom, a nickel atom, a tin atom, a zinc atom, an yttrium atom, an iron atom, an indium atom, a gallium atom, an aluminum atom, a titanium atom, a germanium atom, a zirconium atom, a hafnium atom, or a silicon atom, more preferably a copper atom, a cobalt atom, a nickel atom, or a tin atom because a high-quality thin-film can be produced with satisfactory productivity.

In addition, when the compound is used in a method of producing a thin-film by a MOD method free of any vaporization step, $R^1$ to $R^6$ and M may each be arbitrarily selected in accordance with, for example, solubility in a solvent to be used and a thin-film formation reaction.

Preferred specific examples of the alkoxide compound represented by the general formula (1) include Compounds No. 1 to No. 174 below. In Compounds No. 1 to No. 174 below, "Me" represents a methyl group, "Et" represents an ethyl group, and "iPr" represents an isopropyl group.

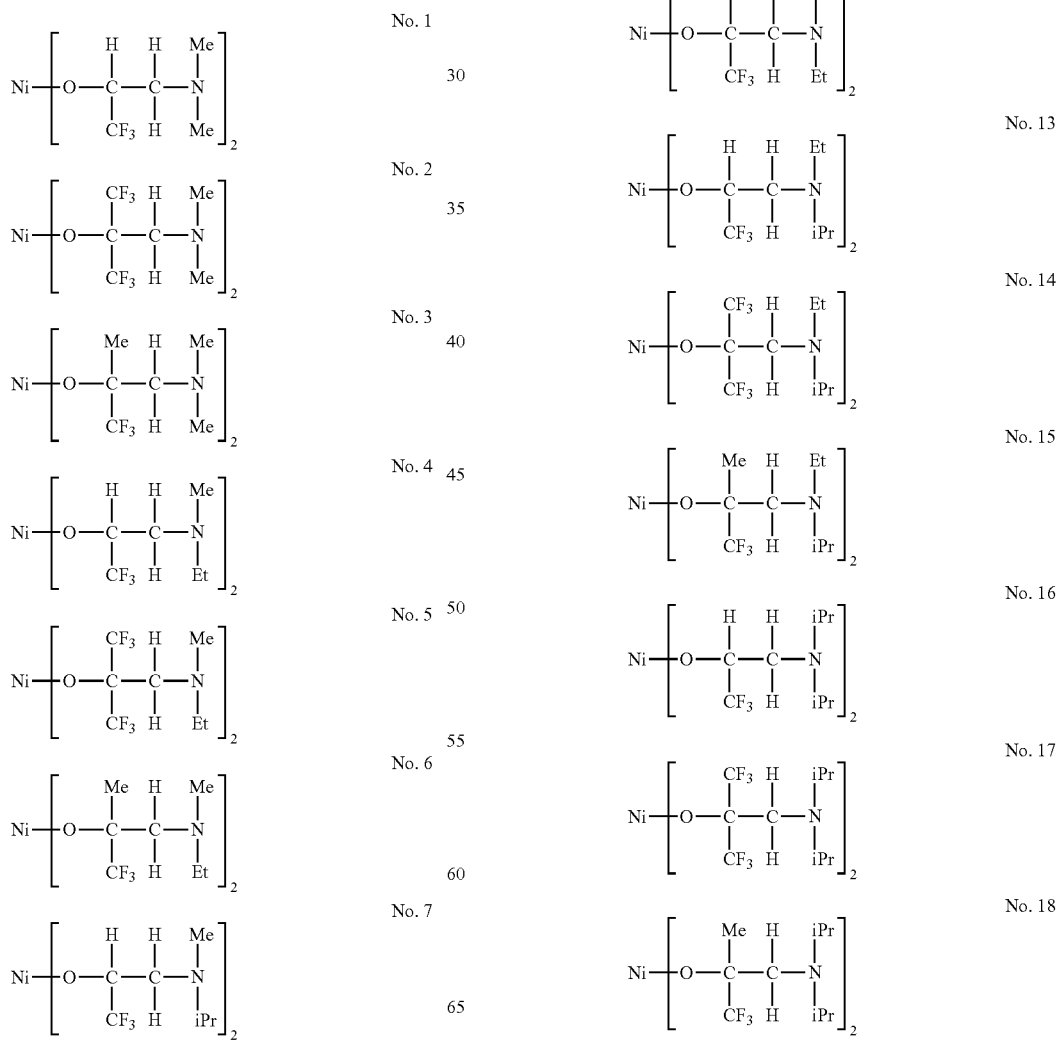

-continued

No. 19:
$$\text{Ni}-\left[\text{O}-\underset{\underset{\text{CF}_3\text{H}_2\text{C}}{|}}{\overset{\overset{\text{H}}{|}}{\text{C}}}-\underset{\underset{\text{H}}{|}}{\overset{\overset{\text{H}}{|}}{\text{C}}}-\underset{\text{Me}}{\overset{\text{Me}}{\text{N}}}\right]_2$$

No. 20:
$$\text{Ni}-\left[\text{O}-\underset{\underset{\text{CF}_3\text{H}_2\text{C}}{|}}{\overset{\overset{\text{CF}_3}{|}}{\text{C}}}-\underset{\underset{\text{H}}{|}}{\overset{\overset{\text{H}}{|}}{\text{C}}}-\underset{\text{Me}}{\overset{\text{Me}}{\text{N}}}\right]_2$$

No. 21:
$$\text{Ni}-\left[\text{O}-\underset{\underset{\text{CF}_3\text{H}_2\text{C}}{|}}{\overset{\overset{\text{Me}}{|}}{\text{C}}}-\underset{\underset{\text{H}}{|}}{\overset{\overset{\text{H}}{|}}{\text{C}}}-\underset{\text{Me}}{\overset{\text{Me}}{\text{N}}}\right]_2$$

No. 22:
$$\text{Ni}-\left[\text{O}-\underset{\underset{\text{CF}_3\text{H}_2\text{C}}{|}}{\overset{\overset{\text{H}}{|}}{\text{C}}}-\underset{\underset{\text{H}}{|}}{\overset{\overset{\text{H}}{|}}{\text{C}}}-\underset{\text{Et}}{\overset{\text{Me}}{\text{N}}}\right]_2$$

No. 23:
$$\text{Ni}-\left[\text{O}-\underset{\underset{\text{CF}_3\text{H}_2\text{C}}{|}}{\overset{\overset{\text{CF}_3}{|}}{\text{C}}}-\underset{\underset{\text{H}}{|}}{\overset{\overset{\text{H}}{|}}{\text{C}}}-\underset{\text{Me}}{\overset{\text{Me}}{\text{N}}}\right]_2$$

No. 24:
$$\text{Ni}-\left[\text{O}-\underset{\underset{\text{CF}_3\text{H}_2\text{C}}{|}}{\overset{\overset{\text{Me}}{|}}{\text{C}}}-\underset{\underset{\text{H}}{|}}{\overset{\overset{\text{H}}{|}}{\text{C}}}-\underset{\text{Et}}{\overset{\text{Me}}{\text{N}}}\right]_2$$

No. 25:
$$\text{Ni}-\left[\text{O}-\underset{\underset{\text{CF}_3\text{H}_2\text{C}}{|}}{\overset{\overset{\text{H}}{|}}{\text{C}}}-\underset{\underset{\text{H}}{|}}{\overset{\overset{\text{H}}{|}}{\text{C}}}-\underset{\text{iPr}}{\overset{\text{Me}}{\text{N}}}\right]_2$$

No. 26:
$$\text{Ni}-\left[\text{O}-\underset{\underset{\text{CF}_3\text{H}_2\text{C}}{|}}{\overset{\overset{\text{CF}_3}{|}}{\text{C}}}-\underset{\underset{\text{H}}{|}}{\overset{\overset{\text{H}}{|}}{\text{C}}}-\underset{\text{iPr}}{\overset{\text{Me}}{\text{N}}}\right]_2$$

No. 27:
$$\text{Ni}-\left[\text{O}-\underset{\underset{\text{CF}_3\text{H}_2\text{C}}{|}}{\overset{\overset{\text{Me}}{|}}{\text{C}}}-\underset{\underset{\text{H}}{|}}{\overset{\overset{\text{H}}{|}}{\text{C}}}-\underset{\text{iPr}}{\overset{\text{Me}}{\text{N}}}\right]_2$$

No. 28:
$$\text{Ni}-\left[\text{O}-\underset{\underset{\text{CF}_3\text{H}_2\text{C}}{|}}{\overset{\overset{\text{H}}{|}}{\text{C}}}-\underset{\underset{\text{H}}{|}}{\overset{\overset{\text{H}}{|}}{\text{C}}}-\underset{\text{Et}}{\overset{\text{Et}}{\text{N}}}\right]_2$$

No. 29:
$$\text{Ni}-\left[\text{O}-\underset{\underset{\text{CF}_3\text{H}_2\text{C}}{|}}{\overset{\overset{\text{CF}_3}{|}}{\text{C}}}-\underset{\underset{\text{H}}{|}}{\overset{\overset{\text{H}}{|}}{\text{C}}}-\underset{\text{Et}}{\overset{\text{Et}}{\text{N}}}\right]_2$$

-continued

No. 30:
$$\text{Ni}-\left[\text{O}-\underset{\underset{\text{CF}_3\text{H}_2\text{C}}{|}}{\overset{\overset{\text{Me}}{|}}{\text{C}}}-\underset{\underset{\text{H}}{|}}{\overset{\overset{\text{H}}{|}}{\text{C}}}-\underset{\text{Et}}{\overset{\text{Et}}{\text{N}}}\right]_2$$

No. 31:
$$\text{Ni}-\left[\text{O}-\underset{\underset{\text{CF}_3\text{H}_2\text{C}}{|}}{\overset{\overset{\text{H}}{|}}{\text{C}}}-\underset{\underset{\text{H}}{|}}{\overset{\overset{\text{H}}{|}}{\text{C}}}-\underset{\text{iPr}}{\overset{\text{Et}}{\text{N}}}\right]_2$$

No. 32:
$$\text{Ni}-\left[\text{O}-\underset{\underset{\text{CF}_3\text{H}_2\text{C}}{|}}{\overset{\overset{\text{CF}_3}{|}}{\text{C}}}-\underset{\underset{\text{H}}{|}}{\overset{\overset{\text{H}}{|}}{\text{C}}}-\underset{\text{iPr}}{\overset{\text{Et}}{\text{N}}}\right]_2$$

No. 33:
$$\text{Ni}-\left[\text{O}-\underset{\underset{\text{CF}_3\text{H}_2\text{C}}{|}}{\overset{\overset{\text{Me}}{|}}{\text{C}}}-\underset{\underset{\text{H}}{|}}{\overset{\overset{\text{H}}{|}}{\text{C}}}-\underset{\text{iPr}}{\overset{\text{Et}}{\text{N}}}\right]_2$$

No. 34:
$$\text{Ni}-\left[\text{O}-\underset{\underset{\text{CF}_3\text{H}_2\text{C}}{|}}{\overset{\overset{\text{H}}{|}}{\text{C}}}-\underset{\underset{\text{H}}{|}}{\overset{\overset{\text{H}}{|}}{\text{C}}}-\underset{\text{iPr}}{\overset{\text{iPr}}{\text{N}}}\right]_2$$

No. 35:
$$\text{Ni}-\left[\text{O}-\underset{\underset{\text{CF}_3\text{H}_2\text{C}}{|}}{\overset{\overset{\text{CF}_3}{|}}{\text{C}}}-\underset{\underset{\text{H}}{|}}{\overset{\overset{\text{iPr}}{|}}{\text{C}}}-\underset{\text{iPr}}{\overset{\text{iPr}}{\text{N}}}\right]_2$$

No. 36:
$$\text{Ni}-\left[\text{O}-\underset{\underset{\text{CF}_3\text{H}_2\text{C}}{|}}{\overset{\overset{\text{Me}}{|}}{\text{C}}}-\underset{\underset{\text{H}}{|}}{\overset{\overset{\text{H}}{|}}{\text{C}}}-\underset{\text{iPr}}{\overset{\text{iPr}}{\text{N}}}\right]_2$$

No. 37:
$$\text{Ni}-\left[\text{O}-\underset{\underset{\text{CF}_3}{|}}{\overset{\overset{\text{H}}{|}}{\text{C}}}-\underset{\underset{\text{H}}{|}}{\overset{\overset{\text{H}}{|}}{\text{C}}}-\underset{\text{Me}}{\overset{\text{Me}}{\text{N}}}\right]_2$$

No. 38:
$$\text{Sn}-\left[\text{O}-\underset{\underset{\text{CF}_3}{|}}{\overset{\overset{\text{CF}_3}{|}}{\text{C}}}-\underset{\underset{\text{H}}{|}}{\overset{\overset{\text{H}}{|}}{\text{C}}}-\underset{\text{Me}}{\overset{\text{Me}}{\text{N}}}\right]_2$$

No. 39:
$$\text{Sn}-\left[\text{O}-\underset{\underset{\text{CF}_3}{|}}{\overset{\overset{\text{Me}}{|}}{\text{C}}}-\underset{\underset{\text{H}}{|}}{\overset{\overset{\text{H}}{|}}{\text{C}}}-\underset{\text{Me}}{\overset{\text{Me}}{\text{N}}}\right]_2$$

No. 40:
$$\text{Sn}-\left[\text{O}-\underset{\underset{\text{CF}_3}{|}}{\overset{\overset{\text{H}}{|}}{\text{C}}}-\underset{\underset{\text{H}}{|}}{\overset{\overset{\text{H}}{|}}{\text{C}}}-\underset{\text{Et}}{\overset{\text{Me}}{\text{N}}}\right]_2$$

No. 41

$$\text{Sn}{-}\left[\text{O}{-}\underset{\underset{\text{CF}_3}{|}}{\overset{\overset{\text{CF}_3}{|}}{\text{C}}}{-}\underset{\underset{\text{H}}{|}}{\overset{\overset{\text{H}}{|}}{\text{C}}}{-}\underset{\underset{\text{Et}}{|}}{\overset{\overset{\text{Me}}{|}}{\text{N}}}\right]_2$$

No. 42

$$\text{Sn}{-}\left[\text{O}{-}\underset{\underset{\text{CF}_3}{|}}{\overset{\overset{\text{Me}}{|}}{\text{C}}}{-}\underset{\underset{\text{H}}{|}}{\overset{\overset{\text{H}}{|}}{\text{C}}}{-}\underset{\underset{\text{Et}}{|}}{\overset{\overset{\text{Me}}{|}}{\text{N}}}\right]_2$$

No. 43

$$\text{Sn}{-}\left[\text{O}{-}\underset{\underset{\text{CF}_3}{|}}{\overset{\overset{\text{H}}{|}}{\text{C}}}{-}\underset{\underset{\text{H}}{|}}{\overset{\overset{\text{H}}{|}}{\text{C}}}{-}\underset{\underset{\text{iPr}}{|}}{\overset{\overset{\text{Me}}{|}}{\text{N}}}\right]_2$$

No. 44

$$\text{Sn}{-}\left[\text{O}{-}\underset{\underset{\text{CF}_3}{|}}{\overset{\overset{\text{CF}_3}{|}}{\text{C}}}{-}\underset{\underset{\text{H}}{|}}{\overset{\overset{\text{H}}{|}}{\text{C}}}{-}\underset{\underset{\text{iPr}}{|}}{\overset{\overset{\text{Me}}{|}}{\text{N}}}\right]_2$$

No. 45

$$\text{Sn}{-}\left[\text{O}{-}\underset{\underset{\text{CF}_3}{|}}{\overset{\overset{\text{Me}}{|}}{\text{C}}}{-}\underset{\underset{\text{H}}{|}}{\overset{\overset{\text{H}}{|}}{\text{C}}}{-}\underset{\underset{\text{iPr}}{|}}{\overset{\overset{\text{Me}}{|}}{\text{N}}}\right]_2$$

No. 46

$$\text{Sn}{-}\left[\text{O}{-}\underset{\underset{\text{CF}_3}{|}}{\overset{\overset{\text{H}}{|}}{\text{C}}}{-}\underset{\underset{\text{H}}{|}}{\overset{\overset{\text{H}}{|}}{\text{C}}}{-}\underset{\underset{\text{Et}}{|}}{\overset{\overset{\text{Et}}{|}}{\text{N}}}\right]_2$$

No. 47

$$\text{Sn}{-}\left[\text{O}{-}\underset{\underset{\text{CF}_3}{|}}{\overset{\overset{\text{CF}_3}{|}}{\text{C}}}{-}\underset{\underset{\text{H}}{|}}{\overset{\overset{\text{H}}{|}}{\text{C}}}{-}\underset{\underset{\text{Et}}{|}}{\overset{\overset{\text{Et}}{|}}{\text{N}}}\right]_2$$

No. 48

$$\text{Sn}{-}\left[\text{O}{-}\underset{\underset{\text{CF}_3}{|}}{\overset{\overset{\text{Me}}{|}}{\text{C}}}{-}\underset{\underset{\text{H}}{|}}{\overset{\overset{\text{H}}{|}}{\text{C}}}{-}\underset{\underset{\text{Et}}{|}}{\overset{\overset{\text{Et}}{|}}{\text{N}}}\right]_2$$

No. 49

$$\text{Sn}{-}\left[\text{O}{-}\underset{\underset{\text{CF}_3}{|}}{\overset{\overset{\text{H}}{|}}{\text{C}}}{-}\underset{\underset{\text{H}}{|}}{\overset{\overset{\text{H}}{|}}{\text{C}}}{-}\underset{\underset{\text{iPr}}{|}}{\overset{\overset{\text{Et}}{|}}{\text{N}}}\right]_2$$

No. 50

$$\text{Sn}{-}\left[\text{O}{-}\underset{\underset{\text{CF}_3}{|}}{\overset{\overset{\text{CF}_3}{|}}{\text{C}}}{-}\underset{\underset{\text{H}}{|}}{\overset{\overset{\text{H}}{|}}{\text{C}}}{-}\underset{\underset{\text{iPr}}{|}}{\overset{\overset{\text{Et}}{|}}{\text{N}}}\right]_2$$

No. 51

$$\text{Sn}{-}\left[\text{O}{-}\underset{\underset{\text{CF}_3}{|}}{\overset{\overset{\text{Me}}{|}}{\text{C}}}{-}\underset{\underset{\text{H}}{|}}{\overset{\overset{\text{H}}{|}}{\text{C}}}{-}\underset{\underset{\text{iPr}}{|}}{\overset{\overset{\text{Et}}{|}}{\text{N}}}\right]_2$$

No. 52

$$\text{Sn}{-}\left[\text{O}{-}\underset{\underset{\text{CF}_3}{|}}{\overset{\overset{\text{H}}{|}}{\text{C}}}{-}\underset{\underset{\text{H}}{|}}{\overset{\overset{\text{H}}{|}}{\text{C}}}{-}\underset{\underset{\text{iPr}}{|}}{\overset{\overset{\text{iPr}}{|}}{\text{N}}}\right]_2$$

No. 53

$$\text{Sn}{-}\left[\text{O}{-}\underset{\underset{\text{CF}_3}{|}}{\overset{\overset{\text{CF}_3}{|}}{\text{C}}}{-}\underset{\underset{\text{H}}{|}}{\overset{\overset{\text{H}}{|}}{\text{C}}}{-}\underset{\underset{\text{iPr}}{|}}{\overset{\overset{\text{iPr}}{|}}{\text{N}}}\right]_2$$

No. 54

$$\text{Sn}{-}\left[\text{O}{-}\underset{\underset{\text{CF}_3}{|}}{\overset{\overset{\text{Me}}{|}}{\text{C}}}{-}\underset{\underset{\text{H}}{|}}{\overset{\overset{\text{H}}{|}}{\text{C}}}{-}\underset{\underset{\text{iPr}}{|}}{\overset{\overset{\text{iPr}}{|}}{\text{N}}}\right]_2$$

No. 55

$$\text{Sn}{-}\left[\text{O}{-}\underset{\underset{\text{CF}_3\text{H}_2\text{C}}{|}}{\overset{\overset{\text{H}}{|}}{\text{C}}}{-}\underset{\underset{\text{H}}{|}}{\overset{\overset{\text{H}}{|}}{\text{C}}}{-}\underset{\underset{\text{Me}}{|}}{\overset{\overset{\text{Me}}{|}}{\text{N}}}\right]_2$$

No. 56

$$\text{Sn}{-}\left[\text{O}{-}\underset{\underset{\text{CF}_3\text{H}_2\text{C}}{|}}{\overset{\overset{\text{CF}_3}{|}}{\text{C}}}{-}\underset{\underset{\text{H}}{|}}{\overset{\overset{\text{H}}{|}}{\text{C}}}{-}\underset{\underset{\text{Me}}{|}}{\overset{\overset{\text{Me}}{|}}{\text{N}}}\right]_2$$

No. 57

$$\text{Sn}{-}\left[\text{O}{-}\underset{\underset{\text{CF}_3\text{H}_2\text{C}}{|}}{\overset{\overset{\text{Me}}{|}}{\text{C}}}{-}\underset{\underset{\text{H}}{|}}{\overset{\overset{\text{H}}{|}}{\text{C}}}{-}\underset{\underset{\text{Me}}{|}}{\overset{\overset{\text{Me}}{|}}{\text{N}}}\right]_2$$

No. 58

$$\text{Sn}{-}\left[\text{O}{-}\underset{\underset{\text{CF}_3\text{H}_2\text{C}}{|}}{\overset{\overset{\text{H}}{|}}{\text{C}}}{-}\underset{\underset{\text{H}}{|}}{\overset{\overset{\text{H}}{|}}{\text{C}}}{-}\underset{\underset{\text{Et}}{|}}{\overset{\overset{\text{Me}}{|}}{\text{N}}}\right]_2$$

No. 59

$$\text{Sn}{-}\left[\text{O}{-}\underset{\underset{\text{CF}_3\text{H}_2\text{C}}{|}}{\overset{\overset{\text{CF}_3}{|}}{\text{C}}}{-}\underset{\underset{\text{H}}{|}}{\overset{\overset{\text{H}}{|}}{\text{C}}}{-}\underset{\underset{\text{Et}}{|}}{\overset{\overset{\text{Me}}{|}}{\text{N}}}\right]_2$$

No. 60

$$\text{Sn}{-}\left[\text{O}{-}\underset{\underset{\text{CF}_3\text{H}_2\text{C}}{|}}{\overset{\overset{\text{Me}}{|}}{\text{C}}}{-}\underset{\underset{\text{H}}{|}}{\overset{\overset{\text{H}}{|}}{\text{C}}}{-}\underset{\underset{\text{Et}}{|}}{\overset{\overset{\text{Me}}{|}}{\text{N}}}\right]_2$$

No. 61

$$\text{Sn}{-}\left[\text{O}{-}\underset{\underset{\text{CF}_3\text{H}_2\text{C}}{|}}{\overset{\overset{\text{H}}{|}}{\text{C}}}{-}\underset{\underset{\text{H}}{|}}{\overset{\overset{\text{H}}{|}}{\text{C}}}{-}\underset{\underset{\text{iPr}}{|}}{\overset{\overset{\text{Me}}{|}}{\text{N}}}\right]_2$$

No. 62

$$\text{Sn}{-}\left[\text{O}{-}\underset{\underset{\text{CF}_3\text{H}_2\text{C}}{|}}{\overset{\overset{\text{CF}_3}{|}}{\text{C}}}{-}\underset{\underset{\text{H}}{|}}{\overset{\overset{\text{H}}{|}}{\text{C}}}{-}\underset{\underset{\text{iPr}}{|}}{\overset{\overset{\text{Me}}{|}}{\text{N}}}\right]_2$$

-continued

No. 63

$$\text{Sn} \left[ \text{O} - \underset{\underset{CF_3H_2C}{|}}{\overset{\overset{Me}{|}}{C}} - \underset{\underset{H}{|}}{\overset{\overset{H}{|}}{C}} - \underset{iPr}{N} \right]_2$$

No. 64

$$\text{Sn} \left[ \text{O} - \underset{\underset{CF_3H_2C}{|}}{\overset{\overset{H}{|}}{C}} - \underset{\underset{H}{|}}{\overset{\overset{H}{|}}{C}} - \underset{Et}{N} \right]_2$$

No. 65

$$\text{Sn} \left[ \text{O} - \underset{\underset{CF_3H_2C}{|}}{\overset{\overset{CF_3}{|}}{C}} - \underset{\underset{H}{|}}{\overset{\overset{H}{|}}{C}} - \underset{Et}{N} \right]_2$$

No. 66

$$\text{Sn} \left[ \text{O} - \underset{\underset{CF_3H_2C}{|}}{\overset{\overset{Me}{|}}{C}} - \underset{\underset{H}{|}}{\overset{\overset{H}{|}}{C}} - \underset{Et}{N} \right]_2$$

No. 67

$$\text{Sn} \left[ \text{O} - \underset{\underset{CF_3H_2C}{|}}{\overset{\overset{H}{|}}{C}} - \underset{\underset{H}{|}}{\overset{\overset{H}{|}}{C}} - \underset{iPr}{N} \right]_2$$

No. 68

$$\text{Sn} \left[ \text{O} - \underset{\underset{CF_3H_2C}{|}}{\overset{\overset{CF_3}{|}}{C}} - \underset{\underset{H}{|}}{\overset{\overset{H}{|}}{C}} - \underset{iPr}{N} \right]_2$$

No. 69

$$\text{Sn} \left[ \text{O} - \underset{\underset{CF_3H_2C}{|}}{\overset{\overset{Me}{|}}{C}} - \underset{\underset{H}{|}}{\overset{\overset{H}{|}}{C}} - \underset{iPr}{N} \right]_2$$

No. 70

$$\text{Sn} \left[ \text{O} - \underset{\underset{CF_3H_2C}{|}}{\overset{\overset{H}{|}}{C}} - \underset{\underset{H}{|}}{\overset{\overset{H}{|}}{C}} - \underset{iPr}{N} \right]_2$$

No. 71

$$\text{Sn} \left[ \text{O} - \underset{\underset{CF_3H_2C}{|}}{\overset{\overset{CF_3}{|}}{C}} - \underset{\underset{H}{|}}{\overset{\overset{H}{|}}{C}} - \underset{iPr}{N} \right]_2$$

No. 72

$$\text{Sn} \left[ \text{O} - \underset{\underset{CF_3H_2C}{|}}{\overset{\overset{Me}{|}}{C}} - \underset{\underset{H}{|}}{\overset{\overset{H}{|}}{C}} - \underset{iPr}{N} \right]_2$$

No. 73

$$\text{Co} \left[ \text{O} - \underset{\underset{CF_3}{|}}{\overset{\overset{H}{|}}{C}} - \underset{\underset{H}{|}}{\overset{\overset{H}{|}}{C}} - \underset{Me}{N} \right]_2$$

No. 74

$$\text{Co} \left[ \text{O} - \underset{\underset{CF_3}{|}}{\overset{\overset{CF_3}{|}}{C}} - \underset{\underset{H}{|}}{\overset{\overset{H}{|}}{C}} - \underset{Me}{N} \right]_2$$

No. 75

$$\text{Co} \left[ \text{O} - \underset{\underset{CF_3}{|}}{\overset{\overset{Me}{|}}{C}} - \underset{\underset{H}{|}}{\overset{\overset{H}{|}}{C}} - \underset{Me}{N} \right]_2$$

No. 76

$$\text{Co} \left[ \text{O} - \underset{\underset{CF_3}{|}}{\overset{\overset{H}{|}}{C}} - \underset{\underset{H}{|}}{\overset{\overset{H}{|}}{C}} - \underset{Et}{N} \right]_2$$

No. 77

$$\text{Co} \left[ \text{O} - \underset{\underset{CF_3}{|}}{\overset{\overset{CF_3}{|}}{C}} - \underset{\underset{H}{|}}{\overset{\overset{H}{|}}{C}} - \underset{Et}{N} \right]_2$$

No. 78

$$\text{Co} \left[ \text{O} - \underset{\underset{CF_3}{|}}{\overset{\overset{Me}{|}}{C}} - \underset{\underset{H}{|}}{\overset{\overset{H}{|}}{C}} - \underset{Et}{N} \right]_2$$

No. 79

$$\text{Co} \left[ \text{O} - \underset{\underset{CF_3}{|}}{\overset{\overset{H}{|}}{C}} - \underset{\underset{H}{|}}{\overset{\overset{H}{|}}{C}} - \underset{iPr}{N} \right]_2$$

No. 80

$$\text{Co} \left[ \text{O} - \underset{\underset{CF_3}{|}}{\overset{\overset{CF_3}{|}}{C}} - \underset{\underset{H}{|}}{\overset{\overset{H}{|}}{C}} - \underset{iPr}{N} \right]_2$$

No. 81

$$\text{Co} \left[ \text{O} - \underset{\underset{CF_3}{|}}{\overset{\overset{Me}{|}}{C}} - \underset{\underset{H}{|}}{\overset{\overset{H}{|}}{C}} - \underset{iPr}{N} \right]_2$$

No. 82

$$\text{Co} \left[ \text{O} - \underset{\underset{CF_3}{|}}{\overset{\overset{H}{|}}{C}} - \underset{\underset{H}{|}}{\overset{\overset{H}{|}}{C}} - \underset{Et}{N} \right]_2$$

No. 83

$$\text{Co} \left[ \text{O} - \underset{\underset{CF_3}{|}}{\overset{\overset{CF_3}{|}}{C}} - \underset{\underset{H}{|}}{\overset{\overset{H}{|}}{C}} - \underset{Et}{N} \right]_2$$

No. 84

$$\text{Co} \left[ \text{O} - \underset{\underset{CF_3}{|}}{\overset{\overset{Me}{|}}{C}} - \underset{\underset{H}{|}}{\overset{\overset{H}{|}}{C}} - \underset{Et}{N} \right]_2$$

No. 85

$$\text{Co}\left[\text{O}-\underset{\underset{\text{CF}_3}{|}}{\overset{\overset{\text{H}}{|}}{\text{C}}}-\underset{\underset{\text{H}}{|}}{\overset{\overset{\text{H}}{|}}{\text{C}}}-\underset{\text{iPr}}{\overset{\text{Et}}{\text{N}}}\right]_2$$

No. 86

$$\text{Co}\left[\text{O}-\underset{\underset{\text{CF}_3}{|}}{\overset{\overset{\text{CF}_3}{|}}{\text{C}}}-\underset{\underset{\text{H}}{|}}{\overset{\overset{\text{H}}{|}}{\text{C}}}-\underset{\text{iPr}}{\overset{\text{Et}}{\text{N}}}\right]_2$$

No. 87

$$\text{Co}\left[\text{O}-\underset{\underset{\text{CF}_3}{|}}{\overset{\overset{\text{Me}}{|}}{\text{C}}}-\underset{\underset{\text{H}}{|}}{\overset{\overset{\text{H}}{|}}{\text{C}}}-\underset{\text{iPr}}{\overset{\text{Et}}{\text{N}}}\right]_2$$

No. 88

$$\text{Co}\left[\text{O}-\underset{\underset{\text{CF}_3}{|}}{\overset{\overset{\text{H}}{|}}{\text{C}}}-\underset{\underset{\text{H}}{|}}{\overset{\overset{\text{H}}{|}}{\text{C}}}-\underset{\text{iPr}}{\overset{\text{iPr}}{\text{N}}}\right]_2$$

No. 89

$$\text{Co}\left[\text{O}-\underset{\underset{\text{CF}_3}{|}}{\overset{\overset{\text{CF}_3}{|}}{\text{C}}}-\underset{\underset{\text{H}}{|}}{\overset{\overset{\text{H}}{|}}{\text{C}}}-\underset{\text{iPr}}{\overset{\text{iPr}}{\text{N}}}\right]_2$$

No. 90

$$\text{Co}\left[\text{O}-\underset{\underset{\text{CF}_3}{|}}{\overset{\overset{\text{Me}}{|}}{\text{C}}}-\underset{\underset{\text{H}}{|}}{\overset{\overset{\text{H}}{|}}{\text{C}}}-\underset{\text{iPr}}{\overset{\text{iPr}}{\text{N}}}\right]_2$$

No. 91

$$\text{Co}\left[\text{O}-\underset{\underset{\text{CF}_3\text{H}_2\text{C}}{|}}{\overset{\overset{\text{H}}{|}}{\text{C}}}-\underset{\underset{\text{H}}{|}}{\overset{\overset{\text{H}}{|}}{\text{C}}}-\underset{\text{Me}}{\overset{\text{Me}}{\text{N}}}\right]_2$$

No. 92

$$\text{Co}\left[\text{O}-\underset{\underset{\text{CF}_3\text{H}_2\text{C}}{|}}{\overset{\overset{\text{CF}_3}{|}}{\text{C}}}-\underset{\underset{\text{H}}{|}}{\overset{\overset{\text{H}}{|}}{\text{C}}}-\underset{\text{Me}}{\overset{\text{Me}}{\text{N}}}\right]_2$$

No. 93

$$\text{Co}\left[\text{O}-\underset{\underset{\text{CF}_3\text{H}_2\text{C}}{|}}{\overset{\overset{\text{Me}}{|}}{\text{C}}}-\underset{\underset{\text{H}}{|}}{\overset{\overset{\text{H}}{|}}{\text{C}}}-\underset{\text{Me}}{\overset{\text{Me}}{\text{N}}}\right]_2$$

No. 94

$$\text{Co}\left[\text{O}-\underset{\underset{\text{CF}_3\text{H}_2\text{C}}{|}}{\overset{\overset{\text{H}}{|}}{\text{C}}}-\underset{\underset{\text{H}}{|}}{\overset{\overset{\text{H}}{|}}{\text{C}}}-\underset{\text{Et}}{\overset{\text{Me}}{\text{N}}}\right]_2$$

No. 95

$$\text{Co}\left[\text{O}-\underset{\underset{\text{CF}_3\text{H}_2\text{C}}{|}}{\overset{\overset{\text{CF}_3}{|}}{\text{C}}}-\underset{\underset{\text{H}}{|}}{\overset{\overset{\text{H}}{|}}{\text{C}}}-\underset{\text{Et}}{\overset{\text{Me}}{\text{N}}}\right]_2$$

No. 96

$$\text{Co}\left[\text{O}-\underset{\underset{\text{CF}_3\text{H}_2\text{C}}{|}}{\overset{\overset{\text{Me}}{|}}{\text{C}}}-\underset{\underset{\text{H}}{|}}{\overset{\overset{\text{H}}{|}}{\text{C}}}-\underset{\text{Et}}{\overset{\text{Me}}{\text{N}}}\right]_2$$

No. 97

$$\text{Co}\left[\text{O}-\underset{\underset{\text{CF}_3\text{H}_2\text{C}}{|}}{\overset{\overset{\text{H}}{|}}{\text{C}}}-\underset{\underset{\text{H}}{|}}{\overset{\overset{\text{H}}{|}}{\text{C}}}-\underset{\text{iPr}}{\overset{\text{Me}}{\text{N}}}\right]_2$$

No. 98

$$\text{Co}\left[\text{O}-\underset{\underset{\text{CF}_3\text{H}_2\text{C}}{|}}{\overset{\overset{\text{CF}_3}{|}}{\text{C}}}-\underset{\underset{\text{H}}{|}}{\overset{\overset{\text{H}}{|}}{\text{C}}}-\underset{\text{iPr}}{\overset{\text{Me}}{\text{N}}}\right]_2$$

No. 99

$$\text{Co}\left[\text{O}-\underset{\underset{\text{CF}_3\text{H}_2\text{C}}{|}}{\overset{\overset{\text{Me}}{|}}{\text{C}}}-\underset{\underset{\text{H}}{|}}{\overset{\overset{\text{H}}{|}}{\text{C}}}-\underset{\text{Me}}{\overset{\text{Me}}{\text{N}}}\right]_2$$

No. 100

$$\text{Co}\left[\text{O}-\underset{\underset{\text{CF}_3\text{H}_2\text{C}}{|}}{\overset{\overset{\text{H}}{|}}{\text{C}}}-\underset{\underset{\text{H}}{|}}{\overset{\overset{\text{H}}{|}}{\text{C}}}-\underset{\text{Et}}{\overset{\text{Et}}{\text{N}}}\right]_2$$

No. 101

$$\text{Co}\left[\text{O}-\underset{\underset{\text{CF}_3\text{H}_2\text{C}}{|}}{\overset{\overset{\text{CF}_3}{|}}{\text{C}}}-\underset{\underset{\text{H}}{|}}{\overset{\overset{\text{H}}{|}}{\text{C}}}-\underset{\text{Et}}{\overset{\text{Et}}{\text{N}}}\right]_2$$

No. 102

$$\text{Co}\left[\text{O}-\underset{\underset{\text{CF}_3\text{H}_2\text{C}}{|}}{\overset{\overset{\text{Me}}{|}}{\text{C}}}-\underset{\underset{\text{H}}{|}}{\overset{\overset{\text{H}}{|}}{\text{C}}}-\underset{\text{Et}}{\overset{\text{Et}}{\text{N}}}\right]_2$$

No. 103

$$\text{Co}\left[\text{O}-\underset{\underset{\text{CF}_3\text{H}_2\text{C}}{|}}{\overset{\overset{\text{H}}{|}}{\text{C}}}-\underset{\underset{\text{H}}{|}}{\overset{\overset{\text{H}}{|}}{\text{C}}}-\underset{\text{iPr}}{\overset{\text{Et}}{\text{N}}}\right]_2$$

No. 104

$$\text{Co}\left[\text{O}-\underset{\underset{\text{CF}_3\text{H}_2\text{C}}{|}}{\overset{\overset{\text{CF}_3}{|}}{\text{C}}}-\underset{\underset{\text{H}}{|}}{\overset{\overset{\text{H}}{|}}{\text{C}}}-\underset{\text{iPr}}{\overset{\text{Et}}{\text{N}}}\right]_2$$

No. 105

$$\text{Co}\left[\text{O}-\underset{\underset{\text{CF}_3\text{H}_2\text{C}}{|}}{\overset{\overset{\text{Me}}{|}}{\text{C}}}-\underset{\underset{\text{H}}{|}}{\overset{\overset{\text{H}}{|}}{\text{C}}}-\underset{\text{iPr}}{\overset{\text{Et}}{\text{N}}}\right]_2$$

No. 106

$$\text{Co}\left[\text{O}-\underset{\underset{\text{CF}_3\text{H}_2\text{C}}{|}}{\overset{\overset{\text{H}}{|}}{\text{C}}}-\underset{\underset{\text{H}}{|}}{\overset{\overset{\text{H}}{|}}{\text{C}}}-\underset{\text{iPr}}{\overset{\text{iPr}}{\text{N}}}\right]_2$$

No. 107

$$\text{Co} \left[ \text{O} - \underset{\underset{\text{CF}_3\text{H}_2\text{C}}{|}}{\overset{\overset{\text{CF}_3}{|}}{\text{C}}} - \underset{\underset{\text{H}}{|}}{\overset{\overset{\text{H}}{|}}{\text{C}}} - \underset{\text{iPr}}{\overset{\text{iPr}}{\text{N}}} \right]_2$$

No. 108

$$\text{Co} \left[ \text{O} - \underset{\underset{\text{CF}_3\text{H}_2\text{C}}{|}}{\overset{\overset{\text{Me}}{|}}{\text{C}}} - \underset{\underset{\text{H}}{|}}{\overset{\overset{\text{H}}{|}}{\text{C}}} - \underset{\text{iPr}}{\overset{\text{iPr}}{\text{N}}} \right]_2$$

No. 109

$$\text{Cu} \left[ \text{O} - \underset{\underset{\text{CF}_3}{|}}{\overset{\overset{\text{H}}{|}}{\text{C}}} - \underset{\underset{\text{H}}{|}}{\overset{\overset{\text{H}}{|}}{\text{C}}} - \underset{\text{Me}}{\overset{\text{Me}}{\text{N}}} \right]_2$$

No. 110

$$\text{Cu} \left[ \text{O} - \underset{\underset{\text{CF}_3}{|}}{\overset{\overset{\text{H}}{|}}{\text{C}}} - \underset{\underset{\text{H}}{|}}{\overset{\overset{\text{H}}{|}}{\text{C}}} - \underset{\text{Et}}{\overset{\text{Me}}{\text{N}}} \right]_2$$

No. 111

$$\text{Cu} \left[ \text{O} - \underset{\underset{\text{CF}_3}{|}}{\overset{\overset{\text{H}}{|}}{\text{C}}} - \underset{\underset{\text{H}}{|}}{\overset{\overset{\text{H}}{|}}{\text{C}}} - \underset{\text{Et}}{\overset{\text{Et}}{\text{N}}} \right]_2$$

No. 112

$$\text{Cu} \left[ \text{O} - \underset{\underset{\text{CF}_3\text{H}_2\text{C}}{|}}{\overset{\overset{\text{H}}{|}}{\text{C}}} - \underset{\underset{\text{H}}{|}}{\overset{\overset{\text{H}}{|}}{\text{C}}} - \underset{\text{Me}}{\overset{\text{Me}}{\text{N}}} \right]_2$$

No. 113

$$\text{Cu} \left[ \text{O} - \underset{\underset{\text{CF}_3\text{H}_2\text{C}}{|}}{\overset{\overset{\text{H}}{|}}{\text{C}}} - \underset{\underset{\text{H}}{|}}{\overset{\overset{\text{H}}{|}}{\text{C}}} - \underset{\text{Et}}{\overset{\text{Me}}{\text{N}}} \right]_2$$

No. 114

$$\text{Cu} \left[ \text{O} - \underset{\underset{\text{CF}_3\text{H}_2\text{C}}{|}}{\overset{\overset{\text{H}}{|}}{\text{C}}} - \underset{\underset{\text{H}}{|}}{\overset{\overset{\text{H}}{|}}{\text{C}}} - \underset{\text{Et}}{\overset{\text{Et}}{\text{N}}} \right]_2$$

No. 115

$$\text{Ni} \left[ \text{O} - \underset{\underset{\text{CF}_3}{|}}{\overset{\overset{\text{H}}{|}}{\text{C}}} - \underset{\underset{\text{Me}}{|}}{\overset{\overset{\text{H}}{|}}{\text{C}}} - \underset{\text{Me}}{\overset{\text{Me}}{\text{N}}} \right]_2$$

No. 116

$$\text{Ni} \left[ \text{O} - \underset{\underset{\text{CF}_3}{|}}{\overset{\overset{\text{CF}_3}{|}}{\text{C}}} - \underset{\underset{\text{Me}}{|}}{\overset{\overset{\text{H}}{|}}{\text{C}}} - \underset{\text{Me}}{\overset{\text{Me}}{\text{N}}} \right]_2$$

No. 117

$$\text{Ni} \left[ \text{O} - \underset{\underset{\text{CF}_3}{|}}{\overset{\overset{\text{Me}}{|}}{\text{C}}} - \underset{\underset{\text{Me}}{|}}{\overset{\overset{\text{H}}{|}}{\text{C}}} - \underset{\text{Me}}{\overset{\text{Me}}{\text{N}}} \right]_2$$

No. 118

$$\text{Ni} \left[ \text{O} - \underset{\underset{\text{CF}_3}{|}}{\overset{\overset{\text{H}}{|}}{\text{C}}} - \underset{\underset{\text{Me}}{|}}{\overset{\overset{\text{H}}{|}}{\text{C}}} - \underset{\text{Et}}{\overset{\text{Me}}{\text{N}}} \right]_2$$

No. 119

$$\text{Ni} \left[ \text{O} - \underset{\underset{\text{CF}_3}{|}}{\overset{\overset{\text{CF}_3}{|}}{\text{C}}} - \underset{\underset{\text{Me}}{|}}{\overset{\overset{\text{H}}{|}}{\text{C}}} - \underset{\text{Et}}{\overset{\text{Me}}{\text{N}}} \right]_2$$

No. 120

$$\text{Ni} \left[ \text{O} - \underset{\underset{\text{CF}_3}{|}}{\overset{\overset{\text{Me}}{|}}{\text{C}}} - \underset{\underset{\text{Me}}{|}}{\overset{\overset{\text{H}}{|}}{\text{C}}} - \underset{\text{Et}}{\overset{\text{Me}}{\text{N}}} \right]_2$$

No. 121

$$\text{Ni} \left[ \text{O} - \underset{\underset{\text{CF}_3}{|}}{\overset{\overset{\text{H}}{|}}{\text{C}}} - \underset{\underset{\text{Me}}{|}}{\overset{\overset{\text{H}}{|}}{\text{C}}} - \underset{\text{iPr}}{\overset{\text{Me}}{\text{N}}} \right]_2$$

No. 122

$$\text{Ni} \left[ \text{O} - \underset{\underset{\text{CF}_3}{|}}{\overset{\overset{\text{CF}_3}{|}}{\text{C}}} - \underset{\underset{\text{Me}}{|}}{\overset{\overset{\text{H}}{|}}{\text{C}}} - \underset{\text{iPr}}{\overset{\text{Me}}{\text{N}}} \right]_2$$

No. 123

$$\text{Ni} \left[ \text{O} - \underset{\underset{\text{CF}_3}{|}}{\overset{\overset{\text{Me}}{|}}{\text{C}}} - \underset{\underset{\text{Me}}{|}}{\overset{\overset{\text{H}}{|}}{\text{C}}} - \underset{\text{iPr}}{\overset{\text{Me}}{\text{N}}} \right]_2$$

No. 124

$$\text{Ni} \left[ \text{O} - \underset{\underset{\text{CF}_3}{|}}{\overset{\overset{\text{H}}{|}}{\text{C}}} - \underset{\underset{\text{Me}}{|}}{\overset{\overset{\text{H}}{|}}{\text{C}}} - \underset{\text{Et}}{\overset{\text{Et}}{\text{N}}} \right]_2$$

No. 125

$$\text{Ni} \left[ \text{O} - \underset{\underset{\text{CF}_3}{|}}{\overset{\overset{\text{CF}_3}{|}}{\text{C}}} - \underset{\underset{\text{Me}}{|}}{\overset{\overset{\text{H}}{|}}{\text{C}}} - \underset{\text{Et}}{\overset{\text{Et}}{\text{N}}} \right]_2$$

No. 126

$$\text{Ni} \left[ \text{O} - \underset{\underset{\text{CF}_3}{|}}{\overset{\overset{\text{Me}}{|}}{\text{C}}} - \underset{\underset{\text{Me}}{|}}{\overset{\overset{\text{H}}{|}}{\text{C}}} - \underset{\text{Et}}{\overset{\text{Et}}{\text{N}}} \right]_2$$

No. 127

$$\text{Ni} \left[ \text{O} - \underset{\underset{\text{CF}_3}{|}}{\overset{\overset{\text{H}}{|}}{\text{C}}} - \underset{\underset{\text{Me}}{|}}{\overset{\overset{\text{H}}{|}}{\text{C}}} - \underset{\text{iPr}}{\overset{\text{Et}}{\text{N}}} \right]_2$$

No. 128

$$\text{Ni} \left[ \text{O} - \underset{\underset{\text{CF}_3}{|}}{\overset{\overset{\text{CF}_3}{|}}{\text{C}}} - \underset{\underset{\text{Me}}{|}}{\overset{\overset{\text{H}}{|}}{\text{C}}} - \underset{\text{iPr}}{\overset{\text{Et}}{\text{N}}} \right]_2$$

No. 129

$$\text{Ni} \left[ \text{O} - \underset{\underset{\text{CF}_3}{|}}{\overset{\overset{\text{Me}}{|}}{\text{C}}} - \underset{\underset{\text{Me}}{|}}{\overset{\overset{\text{H}}{|}}{\text{C}}} - \underset{\text{iPr}}{\overset{\text{Et}}{\text{N}}} \right]_2$$

-continued

No. 130

Ni—[O—C(H)(CF₃)—C(H)(Me)—N(iPr)(iPr)]₂

No. 131

Ni—[O—C(CF₃)(CF₃)—C(H)(Me)—N(iPr)(iPr)]₂

No. 132

Ni—[O—C(Me)(CF₃)—C(H)(Me)—N(iPr)(iPr)]₂

No. 133

Sn—[O—C(H)(CF₃)—C(H)(Me)—N(Me)(Me)]₂

No. 134

Sn—[O—C(CF₃)(CF₃)—C(H)(Me)—N(Me)(Me)]₂

No. 135

Sn—[O—C(Me)(CF₃)—C(H)(Me)—N(Me)(Me)]₂

No. 136

Sn—[O—C(H)(CF₃)—C(H)(Me)—N(Me)(Et)]₂

No. 137

Sn—[O—C(CF₃)(CF₃)—C(H)(Me)—N(Me)(Et)]₂

No. 138

Sn—[O—C(Me)(CF₃)—C(H)(Me)—N(Me)(Et)]₂

No. 139

Sn—[O—C(H)(CF₃)—C(H)(Me)—N(Me)(iPr)]₂

No. 140

Sn—[O—C(CF₃)(CF₃)—C(H)(Me)—N(Me)(iPr)]₂

No. 141

Sn—[O—C(Me)(CF₃)—C(H)(Me)—N(Me)(iPr)]₂

-continued

No. 142

Sn—[O—C(H)(CF₃)—C(H)(Me)—N(Et)(Et)]₂

No. 143

Sn—[O—C(CF₃)(CF₃)—C(H)(Me)—N(Et)(Et)]₂

No. 144

Sn—[O—C(Me)(CF₃)—C(H)(Me)—N(Et)(Et)]₂

No. 145

Sn—[O—C(H)(CF₃)—C(H)(Me)—N(Et)(iPr)]₂

No. 146

Sn—[O—C(CF₃)(CF₃)—C(H)(Me)—N(Et)(iPr)]₂

No. 147

Sn—[O—C(Me)(CF₃)—C(H)(Me)—N(Et)(iPr)]₂

No. 148

Sn—[O—C(H)(CF₃)—C(H)(Me)—N(iPr)(iPr)]₂

No. 149

Sn—[O—C(CF₃)(CF₃)—C(H)(Me)—N(iPr)(iPr)]₂

No. 150

Sn—[O—C(Me)(CF₃)—C(H)(Me)—N(iPr)(iPr)]₂

No. 151

Co—[O—C(H)(CF₃)—C(H)(Me)—N(Me)(Me)]₂

No. 152

Co—[O—C(CF₃)(CF₃)—C(H)(Me)—N(Me)(Me)]₂

No. 153

Co—[O—C(Me)(CF₃)—C(H)(Me)—N(Me)(Me)]₂

-continued

No. 154
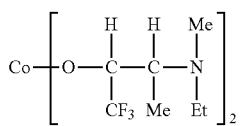

No. 155
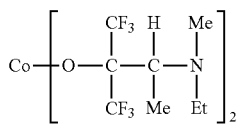

No. 156
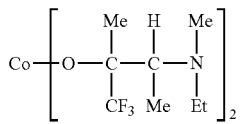

No. 157
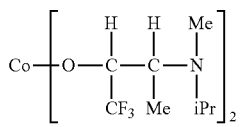

No. 158
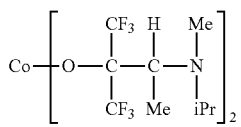

No. 159
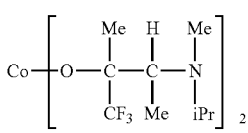

No. 160
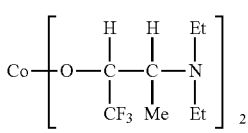

No. 161
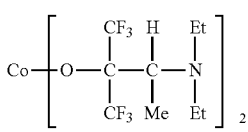

No. 162
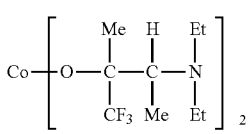

No. 163
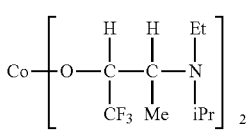

No. 164
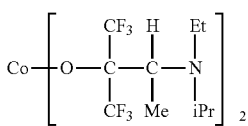

No. 165
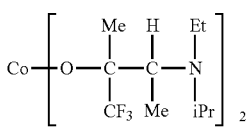

-continued

No. 166
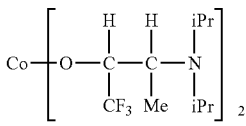

No. 167
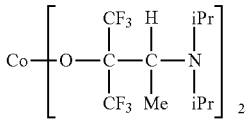

No. 168
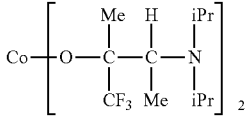

No. 169
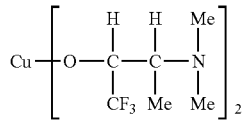

No. 170
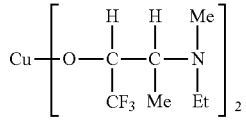

No. 171
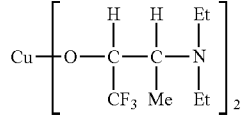

No. 172
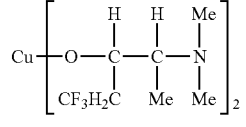

No. 173
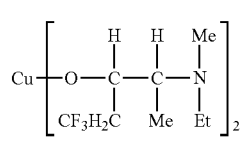

No. 174
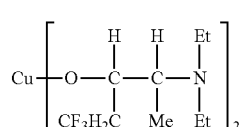

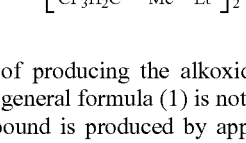

A method of producing the alkoxide compound represented by the general formula (1) is not particularly limited, and the compound is produced by applying a well-known reaction. The compound may be obtained by, for example, causing a metal methoxide complex having a corresponding structure and an alcohol ligand having a corresponding structure to react with each other under a toluene solvent, then distilling off the solvent, and then subjecting the resultant reaction product to distillation purification or sublimation purification.

From the viewpoint of exhibiting desired effects of the present invention, No. 4, No. 40, No. 76, No. 109, and No. 110 alkoxide compounds are preferred, and No. 4, No. 40, No. 76, and No. 110 alkoxide compound are more preferred.

As an alcohol compound that may be utilized for the alcohol ligand, there are given, for example, 3-(dimethylamino) 1,1,1-trifluoropropan-2-ol, 3-(diethylamino)-1,1,1-trifluoropropan-2-ol, 3-(ethylmethylamino)-1,1,1-trifluoropropan-2-ol, 3-(diisopropylamino)-1,1,1-trifluoropropan-2-ol, 2-((dimethylamino)methyl)-1,1,1,3,3,3-hexafluoropropan-2-ol, 2-((diethylamino)methyl)-1,1,1,3,3,3-hexafluoropropan-2-ol, 2-((ethylmethylamino)methyl)-1,1,1,3,3,3-hexafluoropropan-2-ol, and 2-((diisopropylamino)methyl)-1,1,1,3,3,3-hexafluoropropan-2-ol.

Next, a thin-film forming raw material of the present invention is described. The thin-film forming raw material of the present invention contains the alkoxide compound represented by the general formula (1) as a precursor of a thin-film. The form of the thin-film forming raw material varies depending on a production process to which the thin-film forming raw material is applied. For example, when a thin-film containing only a metal atom or a semimetal atom as a metal is produced, the thin-film forming raw material of the present invention is free of a metal compound other than the alkoxide compound represented by the general formula (1) and a semimetal compound. Meanwhile, when a thin-film containing two or more kinds of metals and/or a semimetal is produced, the thin-film forming raw material of the present invention may contain a compound containing a desired metal and/or a compound containing the semimetal (hereinafter sometimes referred to as "other precursor") in addition to the alkoxide compound represented by the general formula (1). The thin-film forming raw material of the present invention may further contain an organic solvent and/or a nucleophilic reagent as described later. As described above, the physical properties of the alkoxide compound represented by the general formula (1) serving as the precursor are suitable for a CVD method, and hence the thin-film forming raw material of the present invention is useful as a chemical vapor deposition raw material (hereinafter sometimes referred to as "CVD raw material"). The thin-film forming raw material of the present invention is particularly suitable for the ALD method out of the CVD methods because the alkoxide compound represented by the general formula (1) has an ALD window.

When the thin-film forming raw material of the present invention is a chemical vapor deposition raw material, the form thereof is appropriately selected depending on a procedure, such as a transportation and supply method of the CVD method to be used.

As the above-mentioned transportation and supply method, there are given a gas transportation method and a liquid transportation method. The gas transportation method involves heating and/or decompressing the CVD raw material in a container in which the raw material is stored (hereinafter sometimes referred to as "raw material container"), to thereby vaporize the raw material to obtain a raw material gas, and introducing the raw material gas into a film formation chamber (hereinafter sometimes referred to as "deposition reaction portion") having a substrate set therein together with a carrier gas, such as argon, nitrogen, or helium, to be used as required. The liquid transportation method involves transporting the CVD raw material to a vaporization chamber under the state of a liquid or a solution, heating and/or decompressing the raw material in the vaporization chamber, to thereby vaporize the raw material to obtain a raw material gas, and introducing the raw material gas into the film formation chamber. In the case of the gas transportation method, the alkoxide compound represented by the general formula (1) itself may be used as the CVD raw material. In the case of the liquid transportation method, the alkoxide compound represented by the general formula (1) itself or a solution obtained by dissolving the compound in an organic solvent may be used as the CVD raw material. Any such CVD raw material may further contain the other precursor, a nucleophilic reagent, and the like.

In addition, in a multi-component CVD method, there are given a method involving vaporizing and supplying the CVD raw material independently for each component (hereinafter sometimes referred to as "single source method"), and a method involving vaporizing and supplying a mixed raw material obtained by mixing a multi-component raw material with desired composition in advance (hereinafter sometimes referred to as "cocktail source method"). In the case of the cocktail source method, a mixture of the alkoxide compound represented by the general formula (1) and the other precursor or a mixed solution obtained by dissolving the mixture in an organic solvent may be used as the CVD raw material. The mixture or the mixed solution may further contain a nucleophilic reagent and the like.

There is no particular limitation on the above-mentioned organic solvent, and a well-known general organic solvent may be used. Examples of the organic solvent include: acetic acid esters, such as ethyl acetate, butyl acetate, and methoxyethyl acetate; ethers, such as tetrahydrofuran, tetrahydropyran, ethylene glycol dimethyl ether, diethylene glycol dimethyl ether, triethylene glycol dimethyl ether, dibutyl ether, and dioxane; ketones, such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons, such as hexane, cyclohexane, methylcyclohexane, dimethylcyclohexane, ethylcyclohexane, heptane, octane, toluene, and xylene; hydrocarbons each having a cyano group, such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; and pyridine and lutidine. Those organic solvents may be used alone or as a mixture thereof depending on the solubility of a solute, a relationship among the use temperature, boiling point, and flash point of each of the solvents, and the like.

When the thin-film forming raw material of the present invention is a mixed solution with the above-mentioned organic solvent, the amount of the entire precursors in the thin-film forming raw material is preferably from 0.01 mol/liter to 2.0 mol/liter, more preferably from 0.05 mol/liter to 1.0 mol/liter.

When the thin-film forming raw material of the present invention is free of a metal compound other than the alkoxide compound represented by the general formula (1) and a semimetal compound, the amount of the entire precursors herein means the amount of the alkoxide compound represented by the general formula (1). When the thin-film forming raw material of the present invention contains a compound containing another metal and/or a compound containing a semimetal (other precursor) in addition to the alkoxide compound represented by the general formula (1), the amount of the entire precursors herein means the total amount of the alkoxide compound represented by the general formula (1) and the other precursor.

In addition, in the case of the multi-component CVD method, there is no particular limitation on the other precursor to be used together with the alkoxide compound represented by the general formula (1), and a well-known general precursor used in the CVD raw material may be used.

Examples of the other precursor include compounds of one kind or two or more kinds selected from the group consisting of compounds used as organic ligands, such as an alcohol compound, a glycol compound, a β-diketone compound, a cyclopentadiene compound, and an organic amine compound, and silicon or a metal. In addition, examples of the kind of the metal in the precursor include lithium, sodium, potassium, magnesium, calcium, strontium, barium, titanium, zirconium, hafnium, vanadium, tantalum, chromium, molybdenum, tungsten, manganese, iron, cobalt, rhodium, iridium, nickel, palladium, platinum, copper, silver, gold, zinc, aluminum, germanium, tin, lead, antimony, bismuth, yttrium, lanthanum, cerium, praseodymium, neodymium, promethium, samarium, europium, gadolinium, terbium, dysprosium, holmium, erbium, thulium, ytterbium, ruthenium, and lutetium.

Examples of the alcohol compound to be used as the organic ligand in the above-mentioned other precursor include: alkyl alcohols, such as methanol, ethanol, propanol, isopropyl alcohol, butanol, sec-butyl alcohol, isobutyl alcohol, tert-butyl alcohol, pentyl alcohol, isopentyl alcohol, and tert-pentyl alcohol; ether alcohols, such as 2-methoxyethanol, 2-ethoxyethanol, 2-butoxyethanol, 2-(2-methoxyethoxy)ethanol, 2-methoxy-1-methylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-s-butoxy-1,1-diethylethanol, and 3-methoxy-1,1-dimethylpropanol; and dialkylamino alcohols, such as dimethylaminoethanol, ethylmethylaminoethanol, diethylaminoethanol, dimethylamino-2-pentanol, ethylmethylamino-2-pentanol, dimethylamino-2-methyl-2-pentanol, ethylmethylamino-2-methyl-2-pentanol, and diethylamino-2-methyl-2-pentanol.

Examples of the glycol compound to be used as the organic ligand in the above-mentioned other precursor include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, and 2,4-dimethyl-2,4-pentanediol.

Examples of the β-diketone compound to be used as the organic ligand in the above-mentioned other precursor include: alkyl-substituted β-diketones, such as acetylacetone, hexane-2,4-dione, 5-methylhexane-2,4-dione, heptane-2,4-dione, 2-methylheptane-3,5-dione, 5-methylheptane-2,4-dione, 6-methylheptane-2,4-dione, 2,2-dimethylheptane-3,5-dione, 2,6-dimethylheptane-3,5-dione, 2,2,6-trimethylheptane-3,5-dione, 2,2,6,6-tetramethylheptane-3,5-dione, octane-2,4-dione, 2,2,6-trimethyloctane-3,5-dione, 2,6-dimethyloctane-3,5-dione, 2,9-dimethylnonane-4,6-dione, 2-methyl-6-ethyldecane-3,5-dione, and 2,2-dimethyl-6-ethyldecane-3,5-dione; fluorine-substituted alkyl β-diketones, such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; and ether-substituted β-diketones, such as 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

Examples of the cyclopentadiene compound to be used as the organic ligand in the above-mentioned other precursor include cyclopentadiene, methylcyclopentadiene, ethylcyclopentadiene, propylcyclopentadiene, isopropylcyclopentadiene, butylcyclopentadiene, sec-butylcyclopentadiene, isobutylcyclopentadiene, tert-butylcyclopentadiene, dimethylcyclopentadiene, and tetramethylcyclopentadiene.

Examples of the organic amine compound to be used as the organic ligand in the above-mentioned other precursor include methylamine, ethylamine, propylamine, isopropylamine, butylamine, sec-butylamine, tert-butylamine, isobutylamine, dimethylamine, diethylamine, dipropylamine, diisopropylamine, ethylmethylamine, propylmethylamine, and isopropylmethylamine.

The above-mentioned other precursors are known in the art, and production methods therefor are also known. An example of the production methods is given as described below. For example, when the alcohol compound is used as the organic ligand, the precursor may be produced through a reaction between an inorganic salt of the metal described above or a hydrate thereof and an alkali metal alkoxide of the alcohol compound. In this case, examples of the inorganic salt of the metal or the hydrate thereof may include a halide and a nitrate of the metal, and examples of the alkali metal alkoxide may include a sodium alkoxide, a lithium alkoxide, and a potassium alkoxide.

In the case of the single source method, a compound similar to the alkoxide compound represented by the general formula (1) in the behavior of thermal decomposition and/or oxidative decomposition is preferably used as the above-mentioned other precursor. In the case of the cocktail source method, a compound that not only is similar to the alkoxide compound represented by the general formula (1) in the behavior of thermal decomposition and/or oxidative decomposition but also does not cause any change impairing desired characteristics as a precursor through a chemical reaction or the like at the time of mixing is preferably used as the above-mentioned other precursor.

In addition, the thin-film forming raw material of the present invention may contain a nucleophilic reagent as required in order to impart stability to the alkoxide compound represented by the general formula (1) and the other precursor. Examples of the nucleophilic reagent include: ethylene glycol ethers, such as glyme, diglyme, triglyme, and tetraglyme; crown ethers, such as 18-crown-6, dicyclohexyl-18-crown-6, 24-crown-8, dicyclohexyl-24-crown-8, and dibenzo-24-crown-8; polyamines, such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethyleneamine; cyclic polyamines, such as cyclam and cyclen; heterocyclic compounds, such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters, such as methyl acetoacetate, ethyl acetoacetate, and 2-methoxyethyl acetoacetate; and β-diketones, such as acetylacetone, 2,4-hexanedione, 2,4-heptanedione, 3,5-heptanedione, and dipivaloylmethane. The usage amount of each of those nucleophilic reagents is preferably from 0.1 mol to 10 mol, more preferably from 1 mol to 4 mol with respect to 1 mol of the amount of the entire precursors.

The thin-film forming raw material of the present invention is prevented from containing impurity metal elements other than the components forming the raw material, impurity halogens, such as impurity chlorine, and impurity organic substances to the extent possible. The content of each of the impurity metal elements is preferably 100 ppb or less, more preferably 10 ppb or less, and the total content thereof is preferably 1 ppm or less, more preferably 100 ppb or less. In particular, when the raw material is used as a gate insulating film, a gate film, or a barrier layer of an LSI, it is required to reduce the contents of alkali metal elements and alkaline-earth metal elements that influence the electrical characteristics of a thin-film to be obtained. The content of the impurity halogens is preferably 100 ppm or less, more preferably 10 ppm or less, most preferably 1 ppm or less. The total content of the impurity organic substances is preferably 500 ppm or less, more preferably 50 ppm or less, most preferably 10 ppm or less. In addition, moisture causes generation of particles in the chemical vapor deposition raw material and generation of particles during thin-film formation. Accordingly, moisture in each of the precursor, the organic solvent, and the nucleophilic reagent is preferably removed as much as possible before its use. The moisture content of each of the precursor, the organic solvent, and the nucleophilic reagent is preferably 10 ppm or less, more preferably 1 ppm or less.

In addition, it is preferred that the thin-film forming raw material of the present invention be prevented from containing particles to the extent possible in order to reduce or prevent particle contamination of a thin-film to be formed. Specifically, in particle measurement with a light scattering liquid particle detector in a liquid phase, it is preferred that the number of particles larger than 0.3 μm be 100 or less in 1 mL of the liquid phase, it is more preferred that the number of particles larger than 0.2 μm be 1,000 or less in 1 mL of the liquid phase, and it is most preferred that the number of particles larger than 0.2 μm be 100 or less in 1 mL of the liquid phase.

Next, a method of producing a thin-film including using the thin-film forming raw material of the present invention is described. A method of producing a thin-film of the present invention is a CVD method including: introducing a raw material gas obtained by vaporizing the thin-film forming raw material of the present invention and a reactive gas to be used as required into a film formation chamber (treatment atmosphere) having a substrate set therein; and then subjecting the precursor in the raw material gas to decomposition and/or a chemical reaction on the substrate, to thereby grow and deposit the thin-film containing a metal atom or a semimetal atom on the surface of the substrate. There are no particular limitations on a transportation and supply method for the raw material, a deposition method therefor, production conditions, a production apparatus, and the like, and well-known general conditions and methods may be used.

Examples of the above-mentioned reactive gas to be used as required include: oxidizing gases, such as oxygen, ozone, and water vapor; hydrocarbon compounds, such as methane and ethane; reducing gases, such as hydrogen, carbon monoxide, and an organic metal compound; and nitriding gases, such as organic amine compounds including a monoalkylamine, a dialkylamine, a trialkylamine, and an alkylenediamine, hydrazine, and ammonia. Those reactive gases may be used alone or as a mixture thereof. The alkoxide compound represented by the general formula (1) has such a property as to react with a reducing gas or an oxidizing gas in a satisfactory manner, and has such a property as to react with hydrogen, water vapor, or ozone in a particularly satisfactory manner. Accordingly, as the reactive gas, a reducing gas or an oxidizing gas is preferably used, and hydrogen, water vapor, or ozone is particularly preferably used.

In addition, examples of the above-mentioned transportation and supply method include the gas transportation method, the liquid transportation method, the single source method, and the cocktail source method described above.

In addition, examples of the above-mentioned deposition method include: thermal CVD including causing a raw material gas, or the raw material gas and a reactive gas, to react only with heat, to thereby deposit a thin-film; plasma CVD using heat and plasma; optical CVD using heat and light; optical plasma CVD using heat, light, and plasma; and ALD including dividing a deposition reaction of CVD into elementary steps, and performing deposition at a molecular level in a stepwise manner.

As a material for the substrate, there are given, for example: silicon; ceramics, such as silicon nitride, titanium nitride, tantalum nitride, titanium oxide, titanium nitride, ruthenium oxide, zirconium oxide, hafnium oxide, and lanthanum oxide; glass; and metals such as metal cobalt. The shape of the substrate is, for example, a plate shape, a spherical shape, a fibrous shape, or a scaly shape. The surface of the substrate may be planar, or may have a three-dimensional structure such as a trench structure.

In addition, examples of the above-mentioned production conditions include a reaction temperature (substrate temperature), a reaction pressure, and a deposition rate. The reaction temperature is preferably from room temperature to 500° C., more preferably from 150° C. to 350° C. In addition, the reaction pressure is preferably from 10 Pa to an atmospheric pressure in the case of the thermal CVD or the optical CVD, and is preferably from 10 Pa to 2,000 Pa in the case of using plasma.

In addition, the deposition rate may be controlled by the supply conditions (vaporization temperature and vaporization pressure) of the raw material, the reaction temperature, and the reaction pressure. When the deposition rate is large, the characteristics of a thin-film to be obtained may deteriorate. When the deposition rate is small, a problem may occur in productivity. Accordingly, the deposition rate is preferably from 0.01 nm/min to 100 nm/min, more preferably from 1 nm/min to 50 nm/min. In addition, in the case of the ALD method, the deposition rate is controlled by the number of cycles so that a desired film thickness may be obtained.

Further, as the above-mentioned production conditions, there are given a temperature and a pressure when the thin-film forming raw material is vaporized to obtain a raw material gas. The step of vaporizing the thin-film forming raw material to obtain a raw material gas may be performed in the raw material container or in the vaporization chamber. In any case, it is preferred that the thin-film forming raw material of the present invention be evaporated at a temperature of from 0° C. to 150° C. In addition, when the thin-film forming raw material is vaporized to obtain a raw material gas in the raw material container or in the vaporization chamber, the pressure in the raw material container and the pressure in the vaporization chamber are both preferably from 1 Pa to 10,000 Pa.

When the ALD method is adopted, the method of producing a thin-film of the present invention may comprise, in addition to a raw material introduction step of vaporizing the thin-film forming raw material by the above-mentioned transportation and supply method to provide a raw material gas, followed by the introduction of the raw material gas into the film formation chamber, a precursor thin-film formation step of forming a precursor thin-film from the above-mentioned compound in the raw material gas on the surface of the above-mentioned substrate, an evacuation step of evacuating an unreacted compound gas, and a metal or semimetal-containing thin-film formation step of causing the precursor thin-film to chemically react with the reactive gas, to thereby form a thin-film containing a metal or a semimetal on the surface of the substrate.

Now, regarding each step of the ALD method, the case of forming a metal thin-film is described in detail as an example. First, the above-mentioned raw material introduction step is performed. The preferred temperature and pressure when the thin-film forming raw material is turned into a raw material gas are the same as those described in the method of producing a thin-film by the CVD method. Next, the raw material gas introduced into the film formation chamber and the surface of the substrate are brought into contact with each other, and hence the precursor thin-film is formed on the surface of the substrate (precursor thin-film formation step). In this case, heat may be applied by heating the substrate or heating the film formation chamber. The precursor thin-film formed in this step is a thin-film produced from the alkoxide compound represented by the general formula (1) or a thin-film produced by the decomposition and/or reaction of part of the alkoxide compound represented by the general formula (1), and hence has composition different from that of the target metal thin-film. The temperature of the substrate when this step is performed is preferably from room temperature to 500° C., more preferably from 150° C. to 350° C. The pressure of a system (in the film formation chamber) when this step is performed is preferably from 1 Pa to 10,000 Pa, more preferably from 10 Pa to 1,000 Pa.

Next, the unreacted compound gas and a gas generated as a by-product are evacuated from the film formation chamber (evacuation step). It is ideal that the unreacted compound gas and the gas generated as a by-product be completely evacuated from the film formation chamber, but it is not always required that the gases be completely evacuated. As an evacuation method, there are given, for example: a method including purging the inside of the system with an inert gas, such as nitrogen, helium, or argon; a method including performing evacuation by decompressing the inside of the system; and a combination of these methods. The degree of decompression when the decompression is performed is preferably from 0.01 Pa to 300 Pa, more preferably from 0.01 Pa to 100 Pa.

Next, a reducing gas is introduced as the reactive gas into the film formation chamber, and the metal thin-film is formed from the precursor thin-film obtained in the previous precursor thin-film formation step through the action of the reducing gas or the action of the reducing gas and heat (metal-containing thin-film formation step). In this step, the temperature when the heat is applied is preferably from room temperature to 500° C., more preferably from 150° C. to 350° C. The pressure of the system (in the film formation chamber) when this step is performed is preferably from 1 Pa to 10,000 Pa, more preferably from 10 Pa to 1,000 Pa. The alkoxide compound represented by the general formula (1) has satisfactory reactivity with the reducing gas, and hence a high-quality metal thin-film containing less residual carbon can be obtained.

When the ALD method is adopted in the method of producing a thin-film of the present invention as described above, thin-film deposition performed by a series of operations consisting of the above-mentioned raw material introduction step, precursor thin-film formation step, evacuation step, and metal-containing thin-film formation step is defined as one cycle, and this cycle may be repeated a plurality of times until a thin-film having a required film thickness is obtained. In this case, it is preferred that, after one cycle is performed, a compound gas and a reactive gas that are unreacted, and a gas generated as a by-product be evacuated from the deposition reaction portion in the same manner as in the above-mentioned evacuation step, and then the subsequent one cycle be performed.

In addition, in the formation of the metal thin-film by the ALD method, energy, such as plasma, light, or a voltage, may be applied, and a catalyst may be used. There are no particular limitations on the timing for applying the energy and the timing for using the catalyst. The energy may be applied or the catalyst may be used, for example, at the time of introducing the compound gas in the raw material introduction step, at the time of heating in the precursor thin-film formation step or the metal-containing thin-film formation step, at the time of evacuating the inside of the system in the evacuation step, or at the time of introducing the reducing gas in the metal-containing thin-film formation step, or between the above-mentioned respective steps.

In addition, in the method of producing a thin-film of the present invention, after the thin-film deposition, annealing treatment may be performed in an inert atmosphere, an oxidizing atmosphere, or a reducing atmosphere in order to obtain more satisfactory electrical characteristics. When step embedding is required, a reflow step may be provided. The temperature in this case is from 200° C. to 1,000° C., preferably from 250° C. to 500° C.

A well-known ALD apparatus may be used in the method of producing a thin-film of the present invention. Specific examples of the ALD apparatus include an apparatus capable of performing bubbling supply of a precursor as illustrated in FIG. 1 and FIG. 3 and an apparatus including a vaporization chamber as illustrated in FIG. 2 and FIG. 4. Another specific example thereof is an apparatus capable of subjecting the reactive gas to plasma treatment as illustrated in FIG. 3 and FIG. 4. The apparatus is not limited to such single-substrate type apparatus each including a film formation chamber (hereinafter referred to as "deposition reaction portion") as illustrated in FIG. 1 to FIG. 4, and an apparatus capable of simultaneously processing a large number of substrates through use of a batch furnace may also be used. Those apparatus may also be used as CVD apparatus.

A thin-film produced through use of the thin-film forming raw material of the present invention may be formed as desired kinds of thin-films, such as thin-films of a metal, oxide ceramics, nitride ceramics, and glass, by appropriately selecting the other precursor, the reactive gas, and the production conditions. It has been known that the thin-films exhibit electrical characteristics, optical characteristics, and the like, and the thin-films have been applied to various usages. Examples thereof include a metal thin-film, a metal oxide thin-film, a metal nitride thin-film, an alloy, and a metal-containing composite oxide thin-film. Those thin-films have been widely used in the production of, for example, an electrode material for a memory element typified by a DRAM element, a resistance film, a diamagnetic film used for the recording layer of a hard disk, and a catalyst material for a polymer electrolyte fuel cell.

EXAMPLES

The present invention is described in more detail below by way of the Examples, the Comparative Examples, and the Evaluation Examples. However, the present invention is by no means limited by the Examples and the like below.
<Production of Alkoxide Compounds>

The production results of alkoxide compounds are described in Examples 1 to 5 below.

[Example 1] Production of Compound No. 4

In a 100 ml four-necked flask, sodium hydride (0.24 g, 10.0 mmol) was dissolved in dehydrated THF (20 ml) at room temperature. 3-(Ethylmethylamino)-1,1,1-trifluoropropan-2-ol (1.71 g, 10.0 mmol) was added to the solution, and the mixture was stirred at 85° C. for 1 hour, and was then stirred at room temperature for 17 hours. The solution was dropped into nickel (II) hexaammine chloride, and the mixture was stirred at 85° C. for 3 hours, and was then stirred at room temperature for 15 hours. The solvent was distilled off under slightly reduced pressure in an oil bath at 70° C. 20 Milliliters of dehydrated hexane was added to the residue, and the mixture was stirred at room temperature. The mixture was filtered with a G4 ball filter under an inert atmosphere to provide a dark brown liquid. The liquid was subjected to desolvation under slightly reduced pressure in an oil bath at 60° C. After that, a brown solid remaining in the flask was subjected to distillation purification under reduced pressure (from 20 Pa to 30 Pa) to provide 1.55 g (3.88 mmol, yield: 78%) of Compound No. 4, which was a brown crystal, as a distillate.

(Analytical Values)
 (1) Elemental analysis (metal analysis: ICP-AES)
   C: 36.2 mass %, H: 5.4 mass %, F: 28.5 mass %, N: 7.0 mass %, Ni: 14.9 mass %, O: 8.0 mass %
   (theoretical values; C: 36.1 mass %, H: 5.6 mass %, F: 28.6 mass %, N: 7.0 mass %, Ni: 14.7 mass %, O: 8.0 mass %)
 (2) Structural analysis (single crystal X-ray analysis)
   Crystal lattice size: 0.28 mm×0.27 mm×0.21 mm
   Crystal system: monoclinic
   (two molecules in an asymmetric unit, R1=0.0669, wR2=0.1911)
   Lattice parameters:
     a=5.837 Å
     b=8.063 Å
     c=17.49 Å
     β=92.655°
     V=822 Å$^3$

[Example 2] Production of Compound No. 40

In a 100 ml four-necked flask, a tin bis(trimethylsilyl) amide complex (1.92 g, 4.36 mmol) was dissolved in dehydrated toluene (30 ml) at room temperature. 3-(Ethylmethylamino)-1,1,1-trifluoropropan-2-ol (1.49 g, 8.72 mmol) was added to the solution, and the mixture was stirred at room temperature for 22 hours. The solvent was distilled off under slightly reduced pressure in an oil bath at 100° C. After that, a purple viscous liquid remaining in the flask was subjected to distillation purification under reduced pressure (from 20 Pa to 30 Pa) to provide 1.35 g (2.94 mmol, yield: 68%) of Compound No. 40, which was a white crystal, as a distillate.

(Analytical Values)
 (1) Elemental analysis (metal analysis: ICP-AES)
   C: 31.6 mass %, H: 4.6 mass %, F: 24.9 mass %, N: 5.9 mass %, Sn: 26.1 mass %, O: 6.9 mass %
   (theoretical values; C: 31.4 mass %, H: 4.8 mass %, F: 24.8 mass %,
   N: 6.1 mass %, Sn: 25.9 mass %, O: 7.0 mass %)
 (2) $^1$H-NMR (deuterated benzene)
   4.27 ppm (s, 2H), 2.38-1.95 ppm (m, 8H), 1.53 ppm (s, 6H), 0.81 ppm (t, J=6.8 Hz, 6H)

[Example 3] Production of Compound No. 110

0.60 Gram (6.3 mmol) of a copper(II) methoxide complex and 20 ml of dehydrated toluene were loaded into a 100 ml four-necked flask at room temperature, and 3-(ethylmethylamino)-1,1,1-trifluoropropan-2-ol (2.2 g, 13 mmol) was dropped into the mixture under ice cooling, followed by stirring at room temperature for 20 hours. Methanol produced as a by-product and the toluene solvent were distilled off in an oil bath at from 70° C. to 90° C. under slightly reduced pressure. After that, a purple solid remaining in the flask was subjected to sublimation purification under reduced pressure (40 Pa) to provide 2.0 g (5.0 mmol, yield: 79%) of Compound No. 110, which was a purple solid, as a volatile matter.

(Analytical Values)
 (1) Elemental analysis (metal analysis: ICP-AES)
   C: 35.6 mass %, H: 5.4 mass %, F: 28.2 mass %, N: 7.1 mass %, Cu: 15.9 mass %, O: 7.8 mass %
   (theoretical values; C: 35.7 mass %, H: 5.5 mass %, F: 28.2 mass %, N: 7.0 mass %, Cu: 15.7 mass %, O: 7.9 mass %)
 (2) Structural analysis (single crystal X-ray analysis)
   Crystal lattice size: 0.15 mm×0.14 mm×0.11 mm Crystal system: monoclinic
   (two molecules in an asymmetric unit, R1=0.0931, wR2=0.2671) Lattice parameters:
     a=5.866 (7) Å
     b=8.094 (9) Å
     c=17.59 (2) Å
     β=91.923 (13°)
     V=835 (2) Å$^3$

[Example 4] Production of Compound No. 76

In a 100 ml four-necked flask, a cobalt bis(trimethylsilyl) amide complex (1.90 g, 5.01 mmol) was dissolved in dehydrated toluene (30 ml) at room temperature. 3-(Ethylmethylamino)-1,1,1-trifluoropropan-2-ol (1.71 g, 10.0 mmol) was added to the solution, and the mixture was stirred at room temperature for 22 hours. The solvent was distilled off under slightly reduced pressure in an oil bath at 100° C. After that, a purple viscous liquid remaining in the flask was subjected to sublimation purification under reduced pressure (from 20 Pa to 30 Pa) to provide 0.33 g (0.827 mmol, yield: 16%) of Compound No. 76, which was a dark purple solid, as a distillate.

(Analytical Values)
 (1) Elemental analysis (metal analysis: ICP-AES) C: 36.2 mass %, H: 5.4 mass %, F: 28.6 mass %, N: 7.1 mass %, Co: 14.9 mass %, O: 7.8 mass %
   (theoretical values; C: 36.1 mass %, H: 5.6 mass %, F: 28.5 mass %, N: 7.0 mass %, Co: 14.8 mass %, O: 8.0 mass %)
 (2) Structural analysis (ATR method: FT-IR)
   ν=425.80 (m), 480.99 (m), 522.23 (m), 587.55 (w), 618.01 (m), 640.43 (m), 692.77 (m), 793.96 (m), 851.63 (m), 862.70 (m), 916.91 (m), 1,019.39 (m), 1,052.74 (m), 1,080.08 (s), 1,100.28 (s), 1,136.77 (m), 1,178.03 (m), 1,266.04 (m), 1,279.58 (m), 1,309.33 (w), 1,381.41 (w), 1,455.30 (w), 2,826.25 (w), 2,872.25 (w), 2,922.69 (w), 2,986.57 (w) cm$^{-1}$

[Example 5] Production of Compound No. 109

0.60 Gram (6.3 mmol) of a copper(II) methoxide complex and 20 ml of dehydrated toluene were loaded into a 100 ml four-necked flask at room temperature, and 3-(dimethylamino)-1,1,1-trifluoropropan-2-ol (2.0 g, 13 mmol) was dropped into the mixture under ice cooling, followed by stirring at room temperature for 20 hours. Methanol produced as a by-product and the toluene solvent were distilled off in an oil bath at from 70° C. to 90° C. under slightly reduced pressure. After that, a purple solid remaining in the flask was subjected to sublimation purification under reduced pressure (40 Pa) to provide 1.4 g (3.7 mmol, yield: 59%) of Compound No. 109, which was a purple solid, as a volatile matter.
(Analytical Values)
(1) Elemental analysis (metal analysis: ICP-AES)
C: 32.2 mass %, H: 4.5 mass %, F: 30.1 mass %, N: 7.4 mass %, Cu: 17.2 mass %, O: 8.6 mass % (theoretical values; C: 32.0 mass %, H: 4.8 mass %, F: 30.3 mass %, N: 7.5 mass %, Cu: 16.9 mass %, O: 8.5 mass %)
(2) Structural analysis (single crystal X-ray analysis)
Crystal lattice size: 0.31 mm×0.18 mm×0.16 mm
Crystal system: monoclinic
(two molecules in an asymmetric unit, $R^{1=0.0834}$, wR2=0.2527) Lattice parameters:
a=5.771 (10) Å
b=10.64 (2) Å
c=12.07 (2) Å
β=93.28 (3) °
γ=63.91°
V=740 (3) Å$^3$

[Evaluation Examples 1 to 4 and Comparative Evaluation Examples 1 to 4] Thermal Stability Evaluation The compounds of the present invention obtained in Examples 1 to 4 and Comparative Compounds 1 to 4 below were each subjected to the following thermal stability evaluation. In Comparative Compounds 1 to 4 below, "Me" represents a methyl group, "Et" represents an ethyl group, and "tBu" represents a tert-butyl group.
(Thermal Stability Evaluation)

The thermal decomposition start temperature of each of the compounds was measured with a DSC measuring apparatus. A compound having a high thermal decomposition start temperature has high thermal stability, and hence can be judged to be preferred as a thin-film forming raw material. The results are shown in Table 1.

TABLE 1

| | Kind of M | Compound | Thermal decomposition start temperature/° C. |
|---|---|---|---|
| Evaluation Example 1 | Nickel | No. 4 | 290 |
| Comparative Evaluation Example 1 | | Comparative Compound 1 | 250 |
| Evaluation Example 2 | Tin | No. 40 | 330 |
| Comparative Evaluation Example 2 | | Comparative Compound 2 | 300 |
| Evaluation Example 3 | Copper | No. 110 | 240 |
| Comparative Evaluation Example 3 | | Comparative Compound 3 | 200 |
| Evaluation Example 4 | Cobalt | No. 76 | 280 |
| Comparative Evaluation Example 4 | | Comparative Compound 4 | 255 |

As shown in Table 1 above, it was found that Compound No. 4 was a compound having a thermal decomposition start temperature higher than that of Comparative Compound 1. In addition, it was found that Compound No. 40 was a compound having a thermal decomposition start temperature higher than that of Comparative Compound 2. In addition, it was found that Compound No. 110 was a compound having a thermal decomposition start temperature higher than that of Comparative Compound 3. In addition, it was found that Compound No. 76 was a compound having a thermal decomposition start temperature higher than that of Comparative Compound 4. In other words, it was found that the alkoxide compound of the present invention was a compound having a thermal decomposition start temperature higher than that of a conventionally known alkoxide compound.

[Evaluation Examples 5 to 7 and Comparative Evaluation Examples 5 to 7] Vapor Pressure Evaluation The compounds of the present invention obtained in Examples 1 to 3 and Comparative Compounds 1 to 3 were each subjected to the following vapor pressure evaluation.
(Vapor Pressure Evaluation)

The weight of a test compound was measured with a TG-DTA under normal pressure at an Ar flow rate of 100 mL/min and a temperature increase rate of 10° C./min in the scanning temperature range of from 30° C. to 600° C., and the temperature (° C.) at which the weight of the test compound reduced by 50 mass % was evaluated as a "temperature (° C.) at the time of a 50 mass % loss in normal-pressure TG-DTA." With regard to a copper compound, Comparative Compound 3 thermally decomposed, and hence the weight of the test compound was separately measured under a reduced pressure of 10 Torr at an Ar flow rate of 50 mL/min and a temperature increase rate of 10° C./min in the scanning temperature range of from 30° C. to 600° C., and the temperature (° C.) at which the weight of the test compound reduced by 50 mass % was evaluated as a "temperature (° C.) at the time of a 50 mass % loss in reduced-pressure TG-DTA." A compound having a low "temperature (° C.) at the time of a 50 mass % loss in normal-pressure TG-DTA" or a low "temperature (° C.) at

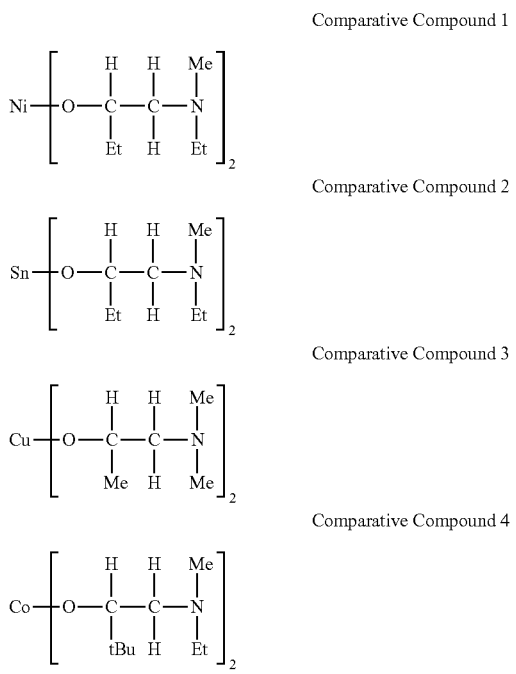

Comparative Compound 1

Comparative Compound 2

Comparative Compound 3

Comparative Compound 4 the time of a 50 mass % loss in reduced-pressure TG-DTA" has a large vapor pressure, and hence can be judged to be preferred as a thin-film forming raw material. The results are shown in Table 2.

TABLE 2

| | Kind of M | Compound | Temperature at the time of 50 mass % loss in normal-pressure (reduced-pressure) TG-DTA [° C.] |
|---|---|---|---|
| Evaluation Example 5 | Nickel | No. 4 | 190 |
| Comparative Evaluation Example 5 | | Comparative Compound 1 | 200 |
| Evaluation Example 6 | Tin | No. 40 | 190 |
| Comparative Evaluation Example 6 | | Comparative Compound 2 | 210 |
| Evaluation Example 7 | Copper | No. 110 | 190 (110) |
| Comparative Evaluation Example 7 | | Comparative Compound 3 | Thermal decomposition (115) |

As shown in Table 2 above, it was found that Compound No. 4 was a compound having a temperature at the time of a 50 mass % loss in normal-pressure TG-DTA lower than that of Comparative Compound 1. In addition, it was found that Compound No. 40 was a compound having a temperature at the time of a 50 mass % loss in normal-pressure TG-DTA lower than that of Comparative Compound 2. Comparative Compound 3 thermally decomposed at the time of its normal-pressure TG-DTA measurement, and hence Compound No. 110 and Comparative Compound 3 were each separately evaluated by reduced-pressure TG-DTA. As result, it was found that Compound No. 110 was a compound having a temperature at the time of a 50 mass % loss in reduced-pressure TG-DTA lower than that of Comparative Compound 3. In other words, it was found that the alkoxide compound of the present invention was a compound having a vapor pressure larger than that of a conventionally known alkoxide compound.

[Examples 6 to 10 and Comparative Examples 1 to 4] Production of Metal Thin-Films and Metal Oxide Thin-Films by ALD Method Metal thin-films and metal oxide thin-films were each produced on a silicon substrate by the ALD method under the following conditions through use of an ALD apparatus illustrated in FIG. 1 with each of the compounds of the present invention obtained in Examples 1 to 5 and Comparative Compounds 1 to 4 being used as a chemical vapor deposition raw material. Regarding each of the obtained thin-films, a film thickness was measured by an X-ray reflectivity method and spectroscopic ellipsometry, a compound of the thin-film was identified by an X-ray diffraction method, and the content of carbon in the thin-film was measured by X-ray photoelectron spectroscopy. The results are shown in Table 3.
(Conditions)
  Reaction temperature (substrate temperature): 150° C. to 300° C., reactive gas: hydrogen, water vapor, or ozone
(Steps)
A series of the following steps (1) to (4) was defined as one cycle, and this cycle was repeated 1,000 times:
(1) vapor of a chemical vapor deposition raw material vaporized under the conditions of a raw material container heating temperature of from 50° C. to 150° C. and a raw material container internal pressure of 100 Pa is introduced, and the raw material is deposited at a system pressure of 100 Pa for 30 seconds;
(2) an unreacted raw material is removed through argon purging for 10 seconds;
(3) a reactive gas is introduced and subjected to a reaction at a system pressure of 100 Pa for from 1 second to 30 seconds; and
(4) the unreacted raw material is removed through argon purging for from 10 seconds to 30 seconds.

TABLE 3

| | Chemical vapor deposition raw material | Reactive gas/supply time | Container temperature/ reaction temperature | Compound of thin-film | Thickness of thin-film | Carbon Content in thin-film |
|---|---|---|---|---|---|---|
| Example 6 | No. 4 | Ozone/ 30 seconds | 50° C./250° C. | Nickel (II) oxide | 50 nm | Not detected*[1] |
| Comparative Example 1 | Comparative Compound 1 | Ozone/ 30 seconds | 60° C./250° C. | Nickel (II) oxide | 20 mm | 6 atm % |
| Example 7 | No. 40 | Water vapor/ 1 second | 110° C./200° C. | Tin (II) oxide | 30 mm | Not detected*[1] |
| Comparative Example 2 | Comparative Compound 2 | Water vapor/ 1 second | 100° C./200° C. | Tin (II) oxide | 10 nm | 5 atm % |
| Example 8 | No. 109 | Hydrogen/ 20 seconds | 70° C./150° C. | Metal copper | 40 nm | Not detected*[1] |
| Example 9 | No. 110 | Hydrogen/ 20 seconds | 80° C./150° C. | Metal copper | 30 nm | Not detected*[1] |
| Comparative Example 3 | Comparative Compound 3 | Hydrogen/ 20 seconds | 70° C./150° C. | Metal copper | 20 nm | 5 atm % |
| Example 10 | No. 76 | Ozone/ 20 seconds | 150° C./300° C. | Cobalt (II) oxide | 40 nm | Not detected*[1] |
| Comparative Example 4 | Comparative Compound 4 | Ozone/ 20 seconds | 120° C./300° C. | Cobalt (II) oxide | 20 nm | 5 atm % |

*[1]The detection limit is 0.1 atm %.

While the carbon content in the metal thin-film obtained by the ALD method was 5 atm % or more in each of Comparative Examples 1 to 4, the carbon content was less than the detection limit, that is, 0.1 atm % in each of Examples 6 to 10. In other words, it was shown that the use of the alkoxide compound of the present invention provided a high-quality metal thin-film and a high-quality metal oxide thin-film. In addition, while the thickness of the resultant thin-film was 20 nm or less in each of Comparative Examples 1 to 4, the thickness was 30 nm or more in each of Examples 6 to 10. Accordingly, the use of the alkoxide compound of the present invention provided a metal thin-film and a metal oxide thin-film with high productivity. The foregoing results showed that the alkoxide compound of the present invention was excellent as a chemical vapor deposition raw material.

The invention claimed is:

1. A method for producing a thin-film containing a metal atom or a semimetal atom on the surface of a substrate, comprising:

vaporizing a thin-film forming raw material comprising an alkoxide compound;

introducing the vaporized compound, into a treatment atmosphere; and subjecting the vaporized compound to decomposition and/or a chemical reaction, to thereby form the thin-film containing a metal atom or a semimetal atom on the surface of the substrate, wherein the alkoxide compound is represented by the following general formula (1):

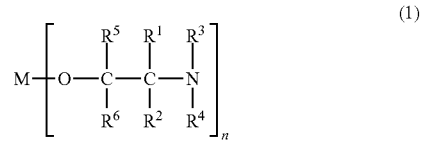

where $R^1$ and $R^2$ each independently represent a hydrogen atom, an alkyl group having 1 to 5 carbon atoms, or a fluorine atom-containing alkyl group having 1 to 5 carbon atoms, $R^3$ and $R^4$ each independently represent an alkyl group having 1 to 5 carbon atoms, or a fluorine atom-containing alkyl group having 1 to 5 carbon atoms, $R^5$ represents a hydrogen atom, a fluorine atom-containing group, or an alkyl group having 1 to 5 carbon atoms, $R^6$ represents a fluorine atom-containing group, M represents a metal atom or a semimetal atom, and "n" represents a valence of the atom represented by M, provided that when M represents a copper atom, $R^3$ and $R^4$ each independently represent an alkyl group having 1 or 2 carbon atoms, and $R^5$ represents a hydrogen atom.

* * * * *